(12) United States Patent
Grubbs et al.

(10) Patent No.: US 7,262,315 B2
(45) Date of Patent: Aug. 28, 2007

(54) TRANSITION METAL OXO, SULFIDO AND AMIDO COMPLEXES AS CATALYSTS OF NUCLEOPHILIC ADDITION REACTIONS

(75) Inventors: Robert H. Grubbs, South Pasadena, CA (US); F. Dean Toste, Berkeley, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/152,957

(22) Filed: May 21, 2002

(65) Prior Publication Data

US 2003/0105306 A1 Jun. 5, 2003

Related U.S. Application Data

(60) Provisional application No. 60/292,822, filed on May 22, 2001, provisional application No. 60/293,269, filed on May 23, 2001.

(51) Int. Cl.
C07F 7/08 (2006.01)
(52) U.S. Cl. ...................... 556/479; 556/482
(58) Field of Classification Search ............... 556/479, 556/482
See application file for complete search history.

(56) References Cited

U.S. PATENT DOCUMENTS

| | | | |
|---|---|---|---|
| 5,342,985 | A | 8/1994 | Herrmann et al. |
| 5,618,958 | A | 4/1997 | Tucker et al. |
| 5,654,455 | A | 8/1997 | Pastor et al. |
| 6,191,065 | B1 | 2/2001 | Williams et al. |
| 6,232,263 | B1 | 5/2001 | Tolleson et al. |
| 6,307,082 | B1 | 10/2001 | Klein et al. |
| 6,326,506 | B1 | 12/2001 | Tachikawa et al. |
| 6,576,772 | B1 * | 6/2003 | Zhang .................. 549/221 |

FOREIGN PATENT DOCUMENTS

WO WO94/17080 * 8/1994

OTHER PUBLICATIONS

Chen et al. (2000), "Investigations of the {ReO}$^{3+}$ Core: A '2 +2' Complex from Bidentate and Potentially Trident Ligands: [ReO(η$^2$-HOC$_6$H$_4$-2-CH$_2$NC$_6$H$_4$S)(η$^2$-SC$_5$H$_4$N)(PPh$_3$)],"*Inorganica Chimica Acta 306*:38-41.
Ciani et al. (1983), "Rhenium(V) Oxide Complexes. Crystal and Molecular Structures of the Compounds *trans*-ReI$_2$O(OR)(PPh$_3$)$_2$ (R=Et, Me) and of Their Hydrolysis Derivative ReIO$_2$(PPh$_3$)$_2$," *Inorganica Chimica Acta 72*:29-37.
Day et al. (1996), "A Diphenylcyclopropene Complex of Tungsten, [WCI$_2$O(PMePh$_2$)$_2$(η$^2$-3,3-di-phenylcyclopropene)], Precursor to a Tungsten-Oxo-Olefin Metathesis Catalyst," *Acta Crystallographica Section C C52*:2460-2462.
de la Mata et al. (1996), "Synthesis and Reactions of Tungsten Oxo vinylalkylidene Complexes: Reactions of WCI$_2$(O)(PX$_3$) (X=OMe, R) Precursors with 3,3-Diphenylcyclopropene," *Organometallics 15*(2):577-584.
Flatt et al. (1994), "Synthesis, Structure, and Reactivity of a Rhenium Oxo-Vinylalkylidene Complex," *Organometallics 13*(7):2728-2732.
Ghosh et al. (1998), "C$_2$-Symmetric Chiral Bis(Oxazoline)-Metal Complexes in Catalytic Asymmetric Synthesis," *Tetrahedron: Asymmetry 9*, pp. 1-45.
Heathcock et al. (1985), "Synthesis and Carbon-Carbon Bond-Forming Reactions of Tungsten, Molybdenum, and Rhenium Enolates," *Pure & Applied Chemistry 57*(12):1789-1798.
Kuz'mina et al. (1986), "Hydrosilylation of 1-Hexene in the Presence," *Bulletin of the Academy of Sciences of the USSR, Division of Chemical Science 35*(1: Part 2):195-198.
Romão et al. (1997), "Rhenium(VII)Oxo and Imido Complexes: Synthesis, Structures, and Applications," *Chemical Reviews 97*(8):3197-3246.
Arias et al. (2001), "Kinetics and Mechanisms of Catalytic Oxygen Atom Transfer with Oxorhenium(V) Oxazoline Complexes," *Inorg. Chem. 20*(9):2185-2192.
Che et al. (1990), "Oxidation of Hydrocarbons by Ruthenium-Oxo Complexes," *Symposium of Oxygen Activation in Catalysis Presented Before the Division of Petroleum Chemistry, Inc. American Chemical Society Boston Meeting*, April 22-27, 1990, pp. 179-186.
Zhesko et al. (1980), "Hydrogenation of Cyclododecatriene on Rhenium Complexes," *Zh. Fiz. Khim*, 54(1):202-203 (abstract only).

* cited by examiner

*Primary Examiner*—Samuel Barts
(74) *Attorney, Agent, or Firm*—Dianne E. Reed; Isaac M. Rutenberg; Mintz, Levin, Cohn, Ferris, Glovsky and Popeo, P.C.

(57) ABSTRACT

Methods are provided for carrying out nucleophilic addition reactions using oxo, sulfido or amido complexes of transition metals as reaction catalysts. Exemplary catalysts are oxo complexes of Group 7 transition metals, with rhenium (V) oxo complexes, including dioxo complexes, preferred. Nucleophilic addition reactions that can be catalyzed using the present methods include silylation, hydrosilylation, hydroamination, silylmetalation, carbometalation, aldol reactions, hydro- and carbometalation initiated cyclization/polymerization, and epoxide/aziridine opening. The invention also pertains to novel transition metal complexes that have utility in catalyzing such reactions.

45 Claims, No Drawings

TRANSITION METAL OXO, SULFIDO AND AMIDO COMPLEXES AS CATALYSTS OF NUCLEOPHILIC ADDITION REACTIONS

CROSS-REFERENCE TO RELATED APPLICATIONS

This application claims priority under 35 U.S.C. §119(e)(1) to Provisional U.S. Patent Applications Ser. Nos. 60/292,822, filed May 22, 2001 and 60/293,269, filed May 23, 2001. The disclosures of the aforementioned applications are incorporated by reference in their entireties.

TECHNICAL FIELD

This invention relates generally to a catalytic method for the addition of nucleophilic reactants to an electrophilic substrate using transition metal oxo, sulfido and amido complexes as catalysts. More particularly, the invention relates to a catalytic method for the addition of silyl groups to unsaturated bonds, using a transition metal-oxo complex as a silylation catalyst for such a reaction.

BACKGROUND OF THE INVENTION

Organosilicon compounds have utility in a wide range of commercial applications. For example, organosilanes are used as precursors to silicon-containing polymers, which, in turn, have numerous uses in the electronics, adhesives, and plastics industries. Organosilanes are also useful in a host of synthetic organic processes, typically as reducing agents and/or silylating agents. Other organosilicon compounds such as hydrolyzable silyl ethers (also termed alkoxysilanes) are used in the manufacture of coatings, glasses, and binders, while less reactive, lower molecular weight silyl ethers find utility as lubricant, heat-transfer, and dielectric fluids.

A well known and widely used reaction for synthesizing organosilicon compounds is the hydrosilylation of olefins, in which a silane reactant $R_3Si-H$ is added to an unsaturated carbon-carbon bond in the presence of a catalyst selected to activate the Si—H bond in the silane precursor. Hydrosilylation of olefins and carbonyl compounds has traditionally been achieved by employing low-valent late transition metal complexes as catalysts, e.g., palladium, platinum, rhodium, and iridium complexes. See Ojima et al., "Recent Advances in the Hydrosilations and Related Reactions," in *The Chemistry of Organic Silicon Compounds*, vol. 2 (New York: Wiley and Sons, 1998), at pages 1687-1792. Illustrative of such catalysts are platinum supported on carbon, chloroplatinic acid, complexes of platinic chloride and unsaturated organic compounds, and compounds and complexes of rhodium, as described, for example, in U.K. Patent Application No. 1,041,237. Also see Chalk (1971), *Ann. N.Y. Acad. Sci.* 172(13):533-540, which describes hydrosilylation of olefins using iridium, platinum and rhodium complexes as hydrosilylation catalysts. Organosilicon compounds have also been synthesized by silylation of carbonyl compounds, including aldehydes and ketones, traditionally using Lewis acid metal complexes as catalysts.

Use of the platinum group metals as hydrosilylation catalysts is, however, problematic in several respects. Complexes of the platinum group metals are typically air- and moisture-sensitive, and, therefore, any reactions catalyzed with such complexes cannot be carried out without taking precautions to avoid air and/or water contamination. These catalysts are also expensive, precluding widespread utility on an industrial scale. In addition, use of highly Lewis acidic complexes as catalysts for the silylation of carbonyl-containing compounds precludes the use of reactants that contain Lewis basic functional groups. Furthermore, in many cases the Lewis acid catalysts are highly intolerant to the presence of water.

Accordingly, there is a need in the art for a new method of catalyzing a silylation reaction that would not be associated with the aforementioned problems. Optimally, then, the catalyst used would be air- and moisture-insensitive, significantly less expensive than the platinum-group catalysts, and tolerant of a range of functional groups. It would also be desirable if such a catalyst were useful in catalyzing stereoselective, e.g., enantioselective, silylation reactions. Furthermore, an ideal catalyst would be useful not only in silylation, but would also be useful in catalyzing other nucleophilic addition reactions wherein a nucleophilic reactant is added to an electrophilic compound containing, as an electrophilic site, an unsaturated carbon-carbon bond, a carbonyl group, a thiocarbonyl group (C=S), or an imino (C=NH) group.

SUMMARY OF THE INVENTION

The present invention is addressed to the aforementioned need in the art, and provides a novel method for catalyzing a nucleophilic addition reaction wherein an electrophilic reactant containing an electrophilic site in the form of an unsaturated bond between a carbon atom and a second atom Q, wherein Q is selected from O, S, N and C, is contacted with a nucleophilic reactant in the presence of a catalytically effective amount of a transition metal oxo, sulfido or amido complex. The reaction is carried out under conditions that provide for nucleophilic addition of the nucleophilic reactant to the electrophilic site of the electrophilic reactant. The transition metal complex that serves as the catalyst has the structure $L_mM(=Z)_n$ wherein:

m is an integer in the range of 2 to 5 inclusive;

n is 1 or 2;

the L groups are ligands, and may be the same or different;

M is a transition metal, preferably selected from Groups 6, 7 and 8 of the Periodic Table of the Elements, with Mo, W, Re, Ru or Os particularly preferred; and Z is O, S or $NR^1$ wherein $R^1$ is hydrogen or hydrocarbyl.

Preferred transition metal complexes are transition metal-oxo complexes in which Z is O. Of the transition metal-oxo complexes, particularly preferred are those complexes wherein n is 2, such that the catalyst is a transition metal-dioxo complex. It will be appreciated that depending on the particular transition metal, number of ligands (m), nature of the ligands (monodentate, bidentate, etc.), and number of (=Z) groups (i.e., n), the complex may be charged and associated with a counterion of opposite charge.

Particularly preferred transition metal complexes are $d_2$-metal-dioxo complexes, which, in contrast to $d_0$-metal-dioxo complexes (e.g., $(CH_3)_3ReO_3$) provide for enhanced Lewis basicity of the oxo ligands, and enhanced Lewis acidity at the metal center. In general, the HOMO (highest occupied molecular orbital) of the present complexes is localized on the oxygen atom of the oxo moieties (or on the sulfur or nitrogen atoms of sulfido or amido moieties, when X is S or NH, respectively), while the LUMO (lowest occupied molecular orbital) is localized on the metal center. In this way, the complexes act as bifunctional catalysts in which the oxo (or sulfido or amido) ligand acts as a Lewis base catalyst and the metal acts as a Lewis acid catalyst. Without wishing to be bound by theory, the preferred $d_2$-metal-dioxo complexes of the invention appear to function as catalysts of a wide variety of nucleophilic addition reactions, in general, by virtue of activating both the nucleophilic and the electrophilic reactants without oxidizing either component. Such reactions include, by way of example, hydrosilylation and other hydrometalation reactions, hydroamination, silylmetalation, carbometalation, aldol reactions, hydro- and carbometalation initiated cyclization/polymerization, and epoxide/aziridine opening. Because the complexes disclosed herein are versatile catalysts useful in catalyzing a wide variety of reactions, it will be appreciated that they may also be used in catalyzing tandem reactions, wherein a first nucleophilic addition reaction results in a product that is also capable of undergoing such a reaction, with each reaction catalyzed by the same complex 0.

While the present method is, accordingly, useful in catalyzing nucleophilic addition reactions in general, a preferred application of the method is in silylation. In this embodiment, the nucleophilic reactant is a silane, and the electrophilic reactant is a compound containing an unsaturated C—C, C—O, C—N, or C—S bond, e.g., an alkene, an alkyne, an aldehyde, a ketone, a thioketone, or an imine.

In the aforementioned silylation reaction, the silane will generally have the structure of formula (I)

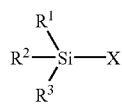
(I)

wherein: $R^1$, $R^2$ and $R^3$ are independently selected from the group consisting of hydrocarbyl, substituted hydrocarbyl, heteroatom-containing hydrocarbyl, and substituted heteroatom-containing hydrocarbyl; and X is hydrogen, cyano, cyanato, azido, alkenyl, alkenyloxy, alkenylthio, or boronato. The electrophilic reactant will generally have the structure of formula (II)

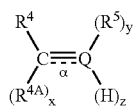
(II)

wherein:
$R^4$, $R^{4A}$ and $R^5$ are independently selected from the group consisting of hydrogen, hydrocarbyl, substituted hydrocarbyl, heteroatom-containing hydrocarbyl, substituted heteroatom-containing hydrocarbyl, and a functional group;
α is an optional bond; and
x, y, and z are zero or 1, with the provisos that (a) when Q is 0 or S, then a is absent, x is 1, and y and z are zero; (b) when Q is N, then a is absent, x and z are 1, and y is zero; (c) when Q is C and α is absent, then x, y and z are 1; and (d) when Q is C and α is present, then x and y are zero and z is 1.

For example, when α is absent, such that the electrophilic reactant has the structure of formula (III)

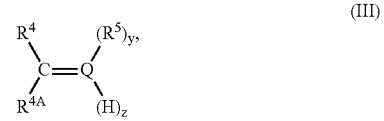
(III)

nucleophilic addition of the silane reactant using a complex of the invention as a catalyst results in a reaction product having the structure of formula (IV)

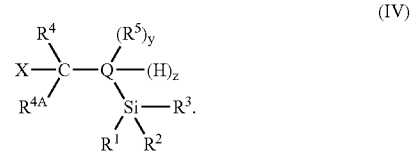
(IV)

In another embodiment, novel transition metal complexes are provided that are useful as catalysts, e.g., in the reaction described above. The novel complexes are transition metal dioxo complexes such as the rhenium (V) dioxo complex having the structure of formula (XV)

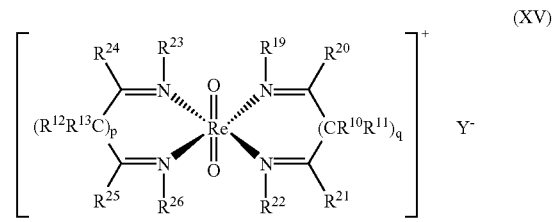
(XV)

wherein:
$Y^-$ is an anion;
p and q are independently zero or 1;
$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups;
$R^{19}$, $R^{22}$, $R^{23}$ and $R^{26}$ are independently selected from the group consisting of hydrocarbyl, substituted hydrocarbyl, heteroatom-containing hydrocarbyl, and substituted heteroatom-containing hydrocarbyl; and
$R^{20}$, $R^{21}$, $R^{24}$ and $R^{25}$ are independently selected from the group consisting of hydrogen, hydrocarbyl, substituted hydrocarbyl, heteroatom-containing hydrocarbyl, and substituted heteroatom-containing hydrocarbyl,
and further wherein any two or more of $R^{19}$, $R^{20}$, $R^{21}$, $R^{22}$, $R^{23}$, $R^{24}$, $R^{25}$ and $R^{26}$ may be taken together to form a cyclic group.

In preferred such complexes, $R^{19}$ and $R^{20}$, $R^{21}$ and $R^{22}$, $R^{23}$ and $R^{24}$, and $R^{25}$ and $R^{26}$ are linked to form cyclic groups, such that the transition metal complex has the structure of formula (XVI)

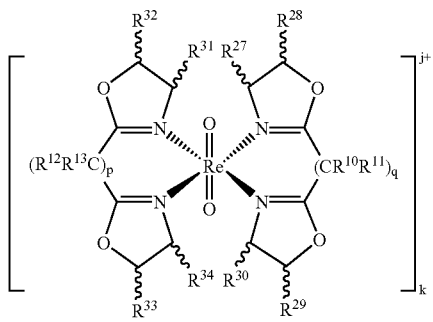

(XVI)

wherein $R^{27}$, $R^{28}$, $R^{29}$, $R^{30}$, $R^{31}$, $R^{32}$, $R^{33}$ and $R^{34}$ are independently selected from the group consisting of hydrogen, $C_1$-$C_{12}$ alkyl, phenyl, and benzyl, or wherein $R^{27}$ and $R^{28}$, $R^{29}$ and $R^{30}$, $R^{31}$ and $R^{32}$, and/or $R^{33}$ and $R^{34}$ are linked to form a cyclic group. The configuration of the $R^{27}$, $R^{28}$, $R^{29}$, $R^{30}$, $R^{31}$, $R^{32}$, $R^{33}$ and $R^{34}$ can be selected so as to provide a chiral complex, such that the complex may be used in catalyzing stereoselective, e.g., enantioselective, reactions.

DETAILED DESCRIPTION OF THE INVENTION

I. Definitions and Nomenclature:

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a functional group" includes a single functional group as well as two or more functional groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched or cyclic alkyl group, where "alkyl" is as defined above.

The term "alkenyl" as used herein refers to a linear, branched or cyclic hydrocarbon group of 2 to 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched or cyclic alkenyl group, where "alkenyl" is as defined above.

The term "alkynyl" as used herein refers to a linear or branched hydrocarbon group of 2 to 20 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain one aromatic ring or 2 to 4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage. An "aryloxy" group may be represented as —O-aryl where aryl is as defined above.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The term "alicyclic" refers to an aliphatic cyclic moiety, which may or may not be bicyclic or polycyclic.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups such as: halo; hydroxyl; sulfhydryl; $C_1$-$C_{20}$ alkoxy; $C_2$-$C_{20}$ alkenyloxy; $C_2$-$C_{20}$ alkynyloxy; $C_5$-$C_{20}$ aryloxy; $C_2$-$C_{20}$ acyl, including $C_2$-$C_{20}$ alkylcarbonyl (—CO-alkyl) and $C_6$-$C_{20}$ arylcarbonyl (—CO-aryl); $C_2$-$C_{20}$ acyloxy, including $C_2$-$C_{20}$ alkoxycarbonyl (—(CO)—O-alkyl) and $C_6$-$C_{20}$ aryloxycarbonyl (—(CO)—O-aryl); halocarbonyl (—CO)—X where X is halo); carboxy (—COOH); carboxylato (—COO$^-$); carbamoyl (—(CO)—NH$_2$); $C_2$-$C_{20}$ alkyl-carbamoyl (—(CO)—NH-alkyl); $C_6$-$C_{20}$ arylcarbamoyl (—(CO)—NH-aryl); thiocarbamoyl (—(CS)—NH$_2$); carbamido (—NH—(CO)—NH$_2$); cyano(—C≡N); isocyano (—N$^+$≡C$^-$); cyanato (—O—C≡N); isocyanato (—O—N$^+$≡C$^-$); isothiocyanato (—S—C≡N); azido (—N=N$^+$=N$^-$); formyl (—(CO)—H); thioformyl (—(CS)—H); amino, including primary amino (—NH$_2$), mono- and di-(alkyl)-substituted amino, and mono- and di-(aryl)-substituted amino; $C_2$-$C_{20}$ alkylamido (—NH—(CO)-alkyl); $C_6$-$C_{20}$ arylamido (—NH—(CO)-aryl); $C_2$-$C_{20}$ imino (—CR=NH where R=hydrogen, alkyl, aryl, alkaryl, etc.); $C_2$-$C_{20}$ alkylimino (—CR=N(alkyl), where R=hydrogen, alkyl, aryl, alkaryl, etc.); arylimino (—CR=N(aryl), where R=hydrogen, alkyl, aryl, alkaryl, etc.); nitro (—NO$_2$); nitroso (—NO); mercapto (—SH); sulfo (—SO$_2$—OH); sulfonato (—SO$_2$—O$^{31}$); $C_1$-$C_{20}$ alkylsulfanyl (—S-alkyl; also termed "alkylthio"); $C_5$-$C_{20}$ arylsulfanyl (—S-aryl; also termed "arylthio"); $C_1$-$C_{20}$ alkylsulfinyl (—(SO)—O-alkyl); $C_5$-$C_{20}$ arylsulfinyl (—(SO)—O-aryl); $C_1$-$C_{20}$ alkylsulfonyl (—SO$_2$—O-alkyl); $C_5$-$C_{20}$ arylsulfonyl (—SO$_2$—O-aryl); thiocarbonyl (=S); boryl (—BH$_2$); borono (—B(OH)$_2$); boronato (—B(OR)$_2$ where R is alkyl or other hydrocarbyl); phosphono (—P(O)(OH)$_2$); phosphonato (—P(O)(O$^-$)$_2$); phosphinato (—P(O)(O$^-$)); phospho (—PO$_2$); and phosphino (—PH$_2$). Suitable substituents also include the hydrocarbyl moieties $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{20}$ aryl (preferably $C_5$-$C_{12}$ aryl), and $C_6$-$C_{20}$ aralkyl (preferably $C_6$-$C_{12}$ aralkyl).

In addition, the aforementioned hydrocarbyl moieties may be further substituted with one or more functional groups or additional hydrocarbyl moieties. Analogously, the above-mentioned functional groups may, if a particular group permits, be further substituted with one or more additional functional groups or with one or more hydrocarbyl moieties such as those specifically enumerated above.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "stereoselective" refers to a chemical reaction that preferentially results in one stereoisomer relative to a second stereoisomer, i.e., gives rise to a product of which the ratio of a desired stereoisomer to a less desired stereoisomer is greater than 1:1. The term "enantioselective" refers to a stereoselective reaction in which the stereoisomers are enantiomers; that is, an enantioselective reaction preferentially results in one enantiomer relative to a second enantiomer.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. Catalysts:

The reactions of the invention are carried out catalytically, using a transition metal oxo, sulfido or amido complex as a catalyst. The transition metal complex that serves as the catalyst has the structure $L_mM(=Z)_n$ wherein:

m is an integer in the range of 2 to 5 inclusive;

n is 1 or 2;

the L groups are ligands, and may be the same or different;

M is a transition metal, preferably selected from Groups 6, 7 and 8 of the Periodic Table of the Elements, with Mo, W, Re, Ru or Os particularly preferred; and Z is O, S or $NR^1$ wherein $R^1$ is hydrogen or hydrocarbyl, and preferred Z moieties are O, such that the complex is a transition metal oxo complex.

The complex may be charged and associated with a counterion of opposite charge, depending on the particular transition metal, number of ligands (m), nature of the ligands (monodentate, bidentate, etc.), and number of (=Z) groups (i.e., n). For example, rhenium (V) complexes are electronically neutral when m is 3, n is 2, and the L groups are monodentate ligands, but bear a positive charge when m is 2, n is 2, and the L groups are bidentate diimine ligands. In the latter case, the complex will be in the form of a salt, i.e., associated with a halide ion or other anion. In one group of preferred complexes: (1) m is 5, n is 1, M is Re, and the L groups are monodentate ligands; (2) m is 4, n is 1, M is Re, one L group is a bidentate ligand, and three L groups are monodentate ligands; and (3) m is 2, n is 2, M is Re, the L groups are bidentate diimine ligands, and the complex is positively charged and associated with an anionic counterion.

Exemplary transition metal complexes for use in conjunction with the methods of the invention have the structure of formula (V)

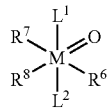
(V)

wherein the various substituents are as follows:

M is a Group 7 transition metal, with Re(V) particularly preferred.

$L^1$ and $L^2$ are neutral electron donor ligands, and may be the same or different. Examples of suitable $L^1$ and $L^2$ moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, $L^1$ and $L^2$ are phosphines of the formula $PR_3$, where each R is independently aryl or $C_1$-$C_{10}$ alkyl, particularly primary alkyl, secondary alkyl or cycloalkyl. In the most preferred embodiments, L is selected from the group consisting of —P(cyclohexyl)$_3$, —P(cyclopentyl)$_3$, —P(isopropyl)$_3$, —P(phenyl)$_3$, —P(phenyl)$_2$($R^4$) and —P(phenyl)($R^4$)$_2$, in which $R^4$ is alkyl, typically lower alkyl. Also preferred are weaker ligands such as the nitrogen-containing heterocycles, which enhance catalytic activity presumably because of the requirement that the L ligand dissociate for initiation to occur.

$R^6$, $R^7$ and $R^8$ are anionic ligands, and may be the same or different, or any two of $R^6$, $R^7$ and $R^8$ may be linked together to form a cyclic group, typically although not necessarily a five- to eight-membered ring, or may be taken together to form a second oxo group =O. In preferred embodiments, $R^6$, $R^7$ and $R^8$ are each independently hydrogen, halide, or one of the following groups: $C_1$-$C_{20}$ alkyl, $C_5$-$C_{20}$ aryl, $C_1$-$C_{20}$ alkoxy, $C_5$-$C_{20}$ aryloxy, $C_3$-$C_{20}$ alkyldiketonate, $C_5$-$C_{20}$ aryldiketonate, $C_2$-$C_{20}$ alkoxycarbonyl, $C_5$-$C_{20}$ aryloxycarbonyl, $C_2$-$C_{20}$ acyl, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl. In more preferred embodiments, $R^6$, $R^7$ and $R^8$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $R^6$, $R^7$ and $R^8$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, phenoxy, methoxy, ethoxy, tosylate, mesylate, or trifluoromethanesulfonate. In the most preferred embodiments, $R^6$, $R^7$ and $R^8$ are each methoxy, ethoxy, chloride or iodide. Optionally, $R^6$, $R^7$ and $R^8$ may be substituted with one or more moieties selected from the group consisting of $C_1$-$C_{12}$ alkyl, $C_1$-$C_{12}$ alkoxy, $C_5$-$C_{20}$ aryl, and halide, which may, in turn, with the exception of halide, be further substituted with one or more groups selected from halide, $C_1$-$C_6$ alkyl, $C_1$-$C_6$ alkoxy, and phenyl. In other preferred embodiments, one of $R^6$, $R^7$ and $R^8$ is as just defined and the other two together form a second oxo moiety.

In another embodiment, the transition metal complex has the structure of formula (VI)

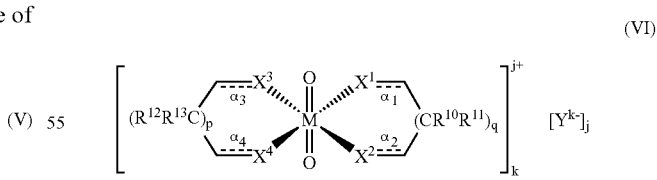
(VI)

wherein:

M is a Group 7 or Group 8 transition metal;

$Y^{-k}$ is anion bearing a charge of $-k$;

either j and k are both 1, or j and k are both 2;

p and q are independently zero or 1;

$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups;

$\alpha_1$, $\alpha_2$, $\alpha_3$ and $\alpha_4$ are optional bonds;

$X^1$, $X^2$, $X^3$ and $X^4$ are independently selected from $NR_{14}$, $NR^{15}R^{16}$ and $PR^{17}R^{18}$, with the proviso that when any of $X^1$, $X^2$, $X^3$ and $X^4$ are $NR^{14}$, then the adjacent $\alpha_1$, $\alpha_2$, $\alpha_3$ or $\alpha_4$ is present and when any of $X^1$, $X^2$, $X^3$ and $X^4$ are $NR^{15}R^{16}$ or $PR^{17}R^{18}$, then the adjacent $\alpha_1$, $\alpha_2$, $\alpha_3$ or $\alpha_4$ is absent; and $R^{14}$, $R^{15}$, $R^{16}$, $R^{17}$ and $R^{18}$ are independently selected from the group consisting of hydrocarbyl, substituted hydrocarbyl, heteroatom-containing hydrocarbyl, and substituted heteroatom-containing hydrocarbyl, and further wherein any two or more of $R^{14}$, $R^{15}$, $R^{16}$, $R^{17}$ and $R^{18}$ may be taken together, optionally with any of $R^{10}$, $R^{11}$, $R^{12}$ and $R^{13}$, to form a cyclic group.

In preferred complexes of formula (VI), M is Re, in which case j and k are 1, or M is Ru or Os, in which case j and k are 2.

It should be appreciated that although the complex of formula (VI) is drawn as a trans-dioxo complex, the structure is intended to encompass cis-dioxo complexes as well, which, technically, have the structure (VIA)

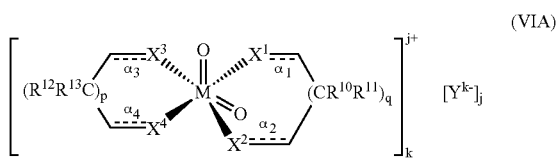

A transition metal complex of formula (VI) containing bidentate diimine ligands will have the structure of formula (VII)

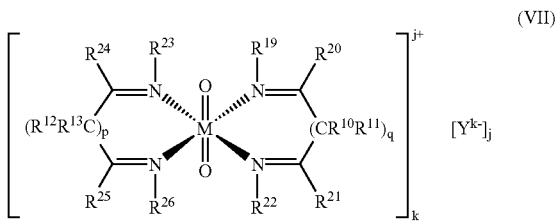

wherein:

$R^{19}$, $R^{22}$, $R^{23}$ and $R^{26}$ are independently selected from the group consisting of hydrocarbyl, substituted hydrocarbyl, heteroatom-containing hydrocarbyl, and substituted heteroatom-containing hydrocarbyl; and $R^{20}$, $R^{21}$, $R^{24}$ and $R^{25}$ are independently selected from the group consisting of hydrogen, hydrocarbyl, substituted hydrocarbyl, heteroatom-containing hydrocarbyl, and substituted heteroatom-containing hydrocarbyl, and further wherein any two or more of $R^{19}$, $R^{20}$, $R^{21}$, $R^{22}$, $R^{23}$, $R^{24}$, $R^{25}$ and $R^{26}$ may be taken together to form a cyclic group.

In preferred complexes of formula (VII), when p and q are 1, $R^{10}$, $R^{11}$, $R^{12}$ and $R^{13}$ are independently selected from the group consisting of hydrogen, $C_1$-$C_{12}$ alkyl, and cyano. For example, $R^{11}$ and $R^{12}$ may be hydrogen, and $R^{11}$ and $R^{13}$ may be cyano or $C_1$-$C_{12}$ alkyl, e.g., methyl. As another example $R^{10}$, $R^{11}$, $R^{12}$ and $R^{13}$ may all be $C_1$-$C_{12}$ alkyl e.g., methyl.

In these complexes, when $R^{19}$ and $R^{20}$, $R^{21}$ and $R^{22}$, $R^{23}$ and $R^{24}$, and $R^{25}$ and $R^{26}$ are linked to form cyclic groups, those cyclic groups may be five- or six-membered rings, or may comprise two or three five- or six-membered rings, which may be either fused or linked. The cyclic groups may be aliphatic or aromatic, and may contain one or more heteroatoms in addition to the nitrogen atoms shown in the structure. In one preferred embodiment, the cyclic groups formed are oxazole groups, with 4,5-dihydrooxazole groups particularly preferred. Such transition metal complex has the structure of formula (VIII)

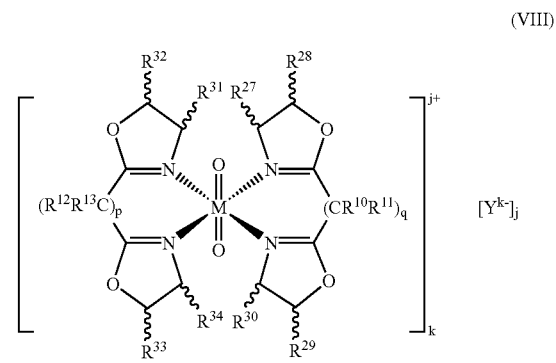

wherein $R^{27}$, $R^{28}$, $R^{29}$, $R^{30}$, $R^{31}$, $R^{32}$, $R^{33}$ and $R^{34}$ are independently selected from the group consisting of hydrogen, $C^1$-$C_{12}$ alkyl, phenyl, and benzyl, or wherein $R^{27}$ and $R^{28}$, $R^{29}$ and $R^{30}$, $R^{31}$ and $R^{32}$, and/or $R^{33}$ and $R^{34}$ are linked to form a cyclic group.

The complex may or not be chiral, depending on the stereochemical configuration of $R^{27}$, $R^{28}$, $R^{29}$, $R^{30}$, $R^{31}$, $R^{32}$, $R^{33}$ and $R^{34}$. To catalyze stereoselective reactions, and enantioselective reactions in particular, the various substituents have the stereochemical configurations indicated in the structure of formula (VIIIA)

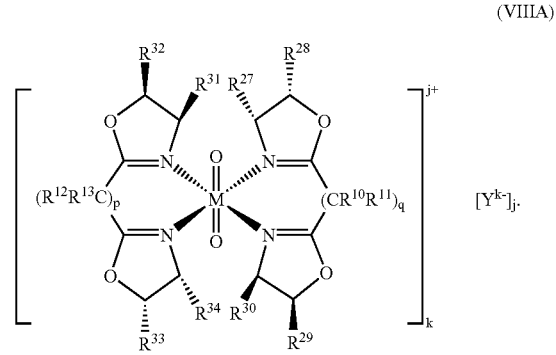

In a variation on such complexes, the ligands are monoanionic, and instead of a second oxo ligand, a water molecule occupies the remaining coordination site, as shown in the structure of formula (VIIIB):

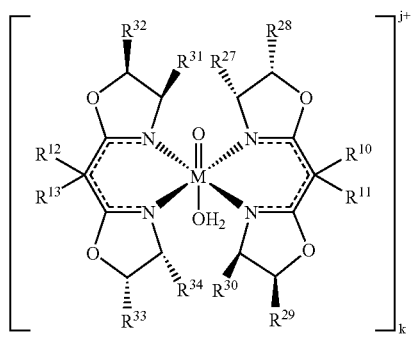

(VIIIB)

In an exemplary complex of formula (IX), M is Re, $R^{10}$, $R^{11}$, $R^{12}$ and $R^{13}$ are independently selected from the group consisting of hydrogen, $C_1$-$C_{12}$ alkyl, and cyano, $R^{28}$, $R^{29}$, $R^{32}$ and $R^{33}$ are hydrogen, and $R^{27}$, $R^{30}$, $R^{31}$ and $R^{34}$ are aryl, e.g., phenyl or benzyl.

In another exemplary complex of formula (IX), M is Re, $R^{10}$, $R^{11}$, $R^{12}$ and $R^{13}$ are independently selected from the group consisting of hydrogen, $C_1$-$C_{12}$ alkyl, and cyano, and $R^{27}$ and $R^{28}$, $R^{29}$ and $R^{30}$, $R^{31}$ and $R^{32}$, and $R^{33}$ and $R^{34}$ are linked to form cyclic groups, such that the complex has the structure of formula (XVIII)

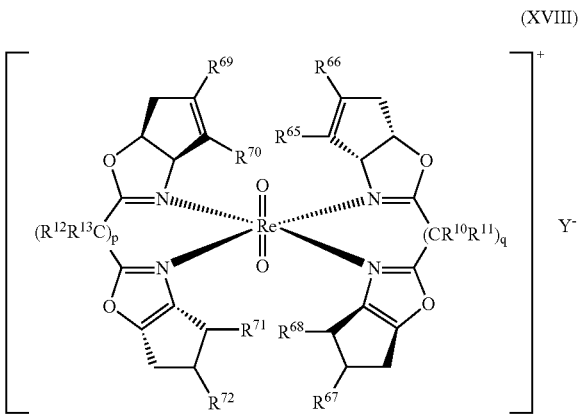

(XVIII)

wherein $R^{65}$, $R^{66}$, $R^{67}$, $R^{68}$, $R^{69}$, $R^{70}$, $R^{71}$ and $R^{72}$ are independently selected from the group consisting of hydrogen, $C_1$-$C_{12}$ alkyl, phenyl, and benzyl, or wherein $R^{65}$ and $R^{66}$, $R^{67}$ and $R^{68}$, $R^{69}$ and $R^{70}$, and $R^{71}$ and $R^{72}$ are linked to form cyclic groups. One example of such a complex is that having the structure of formula (XIX)

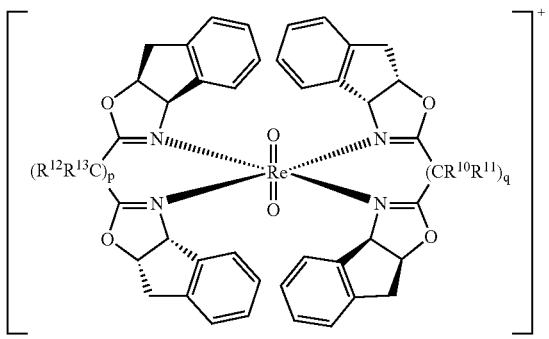

(XIX)

Complexes of formula (VI) are not necessarily diimine-containing complexes, however. As indicated by the definitions of $X^1$, $X^2$, $X^3$ and $X^4$, the ligands may also contain phosphorus and/or oxygen atoms that coordinate to the metal center. In one such complex, $X^1$, $X^2$, $X^3$ and $X^4$ are phosphorus atoms in two bidentate phosphine ligands. Such complexes have the structure of formula (IX)

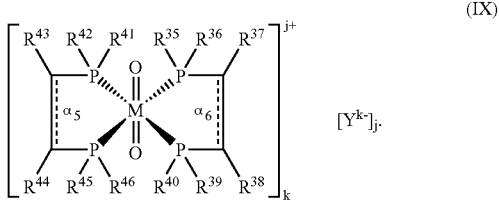

(IX)

wherein:
M is a Group 7 or Group 8 transition metal, preferably a Group 7 transition metal;
$Y^{-k}$ is an anion bearing a charge of –k;
either j and k are both 1, or j and k are both 2;
$\alpha_5$ and $\alpha_6$ are optional bonds;
$R^{35}$, $R^{36}$, $R^{39}$, $R^{40}$, $R^{41}$, $R^{42}$, $R^{45}$ and $R^{46}$ are independently selected from the group consisting of hydrocarbyl, substituted hydrocarbyl, heteroatom-containing hydrocarbyl, and substituted heteroatom-containing hydrocarbyl; and
$R^{37}$, $R^{38}$, $R^{43}$ and $R^{44}$ are independently selected from the group consisting of hydrogen, hydrocarbyl, substituted hydrocarbyl, heteroatom-containing hydrocarbyl, and substituted heteroatom-containing hydrocarbyl,
and further wherein any two or more of $R^{35}$, $R^{36}$, $R^{37}$, $R^{38}$, $R^{39}$, $R^{40}$, $R^{41}$, $R^{42}$, $R^{43}$, $R^{44}$ and $R^{45}$ may be taken together to form a cyclic group.

In a preferred embodiment, M is Re, and j and k are 1, or M is Os or Ru, and j and k are 2. Particularly preferred complexes of formula (IX) are those wherein $\alpha_5$ and $\alpha_6$ are present, and $R^{37}$ and $R^{38}$ taken together, and $R^{43}$ and $R^{44}$ taken together, are phenyl or naphthalenyl. In another preferred embodiment, $\alpha_5$ and $\alpha_6$ are absent, $R^{37}$, $R^{38}$, $R^{43}$ and $R^{44}$ are hydrogen, and $R^{35}$, $R^{36}$, $R^{39}$, $R^{40}$, $R^{41}$, $R^{42}$, $R^{45}$ and $R^{46}$ are aryl, e.g., phenyl.

Other complexes of formula (VI) are Re(V) complexes that contain a coordinating oxygen atom at two or more of $X^1$, $X^2$, $X^3$ and $X^4$. Exemplary such complexes have the structure of formula (X)

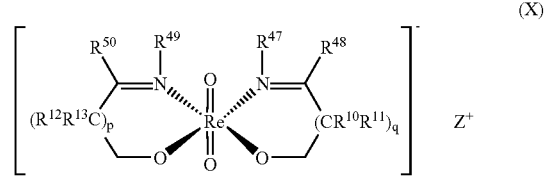

(X)

wherein:
$Z^+$ is a cation;
p and q are independently zero or 1;
$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups;

$R^{47}$ and $R^{48}$ are independently selected from the group consisting of hydrocarbyl, substituted hydrocarbyl, heteroatom-containing hydrocarbyl, and substituted heteroatom-containing hydrocarbyl; and $R^{49}$ and $R^{50}$ are independently selected from the group consisting of hydrogen, hydrocarbyl, substituted hydrocarbyl, heteroatom-containing hydrocarbyl, and substituted heteroatom-containing hydrocarbyl, and further wherein either $R^{47}$ and $R^{49}$, or $R^{47}$ and $R^{48}$ and/or $R^{49}$ and $R^{50}$, may be taken together to form a cyclic group.

As discussed above with respect to complexes of formulae (VII) and (VIII), when $R^{47}$ and $R^{49}$, or $R^{47}$ and $R^{48}$ and/or $R^{49}$ and $R^{50}$, are linked to form cyclic groups, those cyclic groups may be five- or six-membered rings, or may comprise two or three five- or six-membered rings, which may be either fused or linked. The cyclic groups may be aliphatic or aromatic, and may contain one or more heteroatoms in addition to the nitrogen atoms shown in the structure. In one preferred embodiment, the cyclic groups formed are oxazole groups, with 4,5-dihydrooxazole groups particularly preferred.

Still other transition metal oxo complexes useful in the present methods are rhenium complexes having the structure of formula (XI)

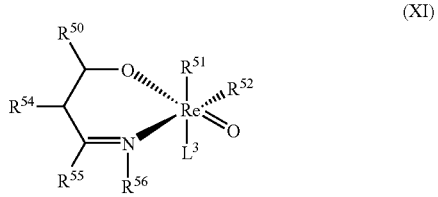

(XI)

wherein:

$L^3$ is a neutral electron donor ligand, and is defined as for $L^1$ and $L^2$;

$R^{51}$ and $R^{52}$ are anionic ligands, and are defined as for $R^6$, $R^7$ and $R^8$;

$R^{53}$, $R^{54}$ and $R^{55}$ are independently selected from the group consisting of hydrogen, hydrocarbyl, substituted hydrocarbyl, heteroatom-containing hydrocarbyl, and substituted heteroatom-containing hydrocarbyl; and $R^{56}$ is selected from the group consisting of hydrocarbyl, substituted hydrocarbyl, heteroatom-containing hydrocarbyl, and substituted heteroatom-containing hydrocarbyl, and further wherein $R^{53}$ and $R^{54}$, and/or $R^{55}$ and $R^{56}$, may be taken together to form a cyclic group.

In exemplary complexes of formula (XI), $R^{53}$ and $R^{54}$ together form a phenyl ring, and $R^{55}$ and $R^{56}$ together form a 4,5-dihydrooxazole ring optionally substituted at the 4-position, such that the structure has the formula (XII)

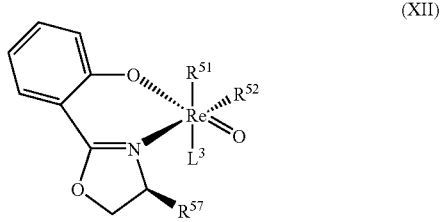

(XII)

wherein:

$L^3$ is P(cyclohexyl)$_3$ or —P(cyclopentyl)$_3$;

$R^{51}$ and $R^{52}$ are halide; and $R^{57}$ is selected from the group consisting of hydrogen, $C_1$-$C_{12}$ alkyl, phenyl, and benzyl.

Still another transition metal oxo complex useful in the present catalytic methods have the structure of formula (XIII)

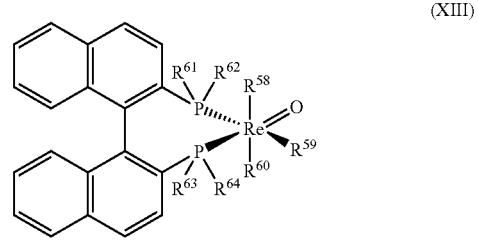

(XIII)

wherein $R^{58}$, $R^{59}$ and $R^{60}$ are halide, and $R^{61}$ and $R^{62}$ are aryl, and the structure of formula (XIV)

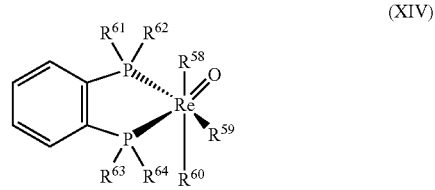

(XIV)

wherein $R^{58}$, $R^{59}$ and $R^{60}$ are halide, and $R^{61}$, $R^{62}$, $R^{63}$ and $R^{64}$ are aryl, or wherein $R^{61}$ and $R^{62}$, and/or $R^{63}$ and $R^{64}$, may be taken together to form a cyclic group.

Complexes of formulae (VII), (VIII), (VIIIA), (VIIIB), (X) through (XIV), (XVIII) and (XIX) are new chemical entities. Particularly preferred novel complexes herein are the dioxo complexes having the structures of formulae (VII), (VIII), and (VIIIA), wherein M is rhenium (V), as follows:

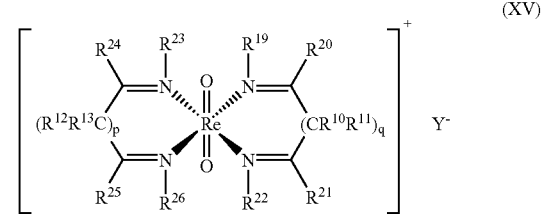

(XV)

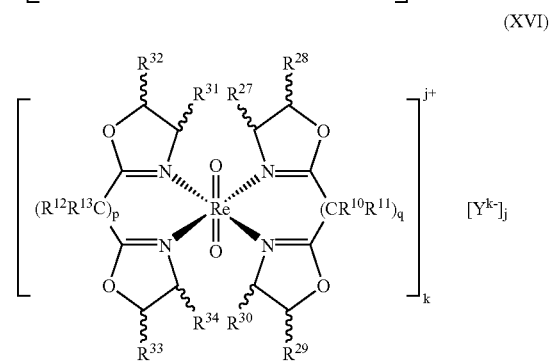

(XVI)

-continued (XVII)

*Structure showing Re complex with substituents $R^{27}$ through $R^{34}$, $R^{10}$, $R^{11}$, $R^{12}$, $R^{13}$, counterion $Y^-$*

In the foregoing structures, j, k, p, q, Y, and the various R groups are as defined herein with respect to the complexes of formulae (VII), (VIII), and (VIIIA).

Those complexes described in this section that are not new chemical entities may be purchased from commercial sources, e.g., Aldrich (Milwaukee Wis.) or Strem Chemicals, Inc. (Newburyport, Mass.). The novel complexes can be synthesized using the general procedures described in the experimental section herein, in Examples 4, 5 and 6, or modifications thereof, as will be appreciated by those of ordinary skill in the art.

III. Reactions:

Prior catalytic applications of transition metal oxo complexes, and transition metal dioxo complexes in particular, involved functional group oxidation and oxygen transfer reactions such as epoxidations and dihydroxylation. In contrast, the transition metal complexes of the invention are now used in the catalysis of nucleophilic addition reactions, wherein the complex serves as a bifunctional catalyst, with the oxo (or sulfido or amido) ligand acting as a Lewis base catalyst and the metal center acting as a Lewis acid catalyst. As such, the complexes of the invention find utility in catalyzing a host of nucleophilic addition reactions, including, but not limited to, hydrosilylation and other hydrometalation reactions, hydroamination, silylmetalation, carbometalation, aldol reactions, hydro- and carbometalation initiated cyclization/polymerization, and epoxide/aziridine opening.

Hydrosilylation and other hydrometalation reactions: Hydride reduction of carbonyl groups represents one of the simplest and most often used reactions in organic chemistry. In many cases, the alcohol produced from the reaction is subsequently protected as a silyl ether. Despite the fact that hydrosilylation of ketones and aldehydes should provide the opportunity to accomplish this transformation in a single operation, those working in the field have encountered numerous obstacles to development of a suitable reaction. Many hydrosilylation reactions have employed low-valent late transition metal catalysts that, by virtue of their low oxidation state, are often air- and moisture-sensitive. Low valent early transition metal metallocene catalysts, which have also been used, suffer from similar problems as well as being incompatible with a variety of Lewis basic functional groups. Furthermore, prior catalytic systems often use polyhydridic silanes and therefore the alcohol and not the silyl ether is isolated. By contrast, the methodology of the invention provides a catalyst system that is air- and moisture-insensitive, has high functional group tolerance, and provides synthetically useful silyl ethers (e.g., t-butyldimethylsilyl, or "TBDMS").

In hydrosilylation, the nucleophilic reactant is a silane, and the electrophilic reactant is a compound containing an unsaturated C—C, C—O, C—N, or C—S bond, e.g., an alkene, an alkyne, an aldehyde, a ketone, a thioketone, or an imine. In hydrosilylation reactions, the silane will generally have the structure of formula (I)

$$R^2-\underset{\underset{R^3}{|}}{\overset{\overset{R^1}{|}}{Si}}-X \qquad (I)$$

wherein $R^1$, $R^2$ and $R^3$ are independently selected from the group consisting of hydrocarbyl, substituted hydrocarbyl, heteroatom-containing hydrocarbyl, and substituted heteroatom-containing hydrocarbyl, and X is hydrogen. The electrophilic reactant has the structure of formula (II)

$$\underset{(R^{4A})_x}{\overset{R^4}{\diagdown}}C\overset{\alpha}{=\!=\!=}Q\underset{(H)_z}{\overset{(R^5)_y}{\diagup}} \qquad (II)$$

wherein:
$R^4$, $R^{4A}$ and $R^5$ are independently selected from the group consisting of hydrogen, hydrocarbyl, substituted hydrocarbyl, heteroatom-containing hydrocarbyl, substituted heteroatom-containing hydrocarbyl, and a functional group;
α is an optional bond; and
x, y, and z are zero or 1, with the provisos that (a) when Q is O or S, then α is absent, x is 1, and y and z are zero; (b) when Q is N, then a is absent, x and z are 1, and y is zero; (c) when Q is C and α is absent, then x, y and z are 1; and (d) when Q is C and α is present, then x and y are zero and z is 1.

When α is absent, such that the electrophilic reactant has the structure of formula (III)

$$\underset{R^{4A}}{\overset{R^4}{\diagdown}}C=Q\underset{(H)_z}{\overset{(R^5)_{y'}}{\diagup}} \qquad (III)$$

nucleophilic addition of the silane reactant using a complex of the invention as a catalyst results in a reaction product having the structure of formula (IV)

$$X-\underset{R^{4A}}{\overset{R^4}{|}}C-\underset{\underset{R^1}{|}\underset{R^2}{|}}{\overset{(R^5)_y}{|}}Q-(H)_z \qquad (IV)$$

It will be appreciated that the reaction is not necessarily limited to hydrosilylation, however, and that other silylation reactions wherein X is other than hydrogen, e.g., cyano, cyanato, azido, alkenyl, alkenyloxy, alkenylthio, or boronato, are also possible, as will be discussed in detail below. Furthermore, the aforementioned reaction is not limited to silicon-containing nucleophiles, and that analogous hydrostannylation and hydroboration reactions will be similarly catalyzed using the present catalysts.

Hydroamination: Transition metal catalyzed hydroamination of olefins and alkynes continues to receive considerable attention. In general, two approaches have been employed: (1) activation of the olefin by complexation to electrophilic transition metals (e.g., Pd(II), Pt(II)), and (2) N—H bond activation by early transition metal, lanthanides and actinides. The methodology of the invention now allows for activation of both an unsaturated reactant and the amine in a hydroamination reaction. Such a reaction will typically involve a silylazide, e.g., a trialkylsilylazide, and an unsaturated reactant in the form of an alkene or alkyne. That is, the silane reactant will have the structure of formula (I), wherein X is azido (—$N_3$) and $R^1$, $R^2$ and $R^3$ are $C_1$-$C_{12}$ alkyl, preferably lower alkyl, and the unsaturated electrophilic reactant will have the structure of formula (II) wherein $R^4$, $R^{4A}$ and $R^5$ are as defined previously, α is an optional bond, and when α is absent, then x, y and z are 1, and α is present, then x and y are zero and z is 1. Reaction with an olefin can serve as an initial step toward the formation of a primary amine, as follows:

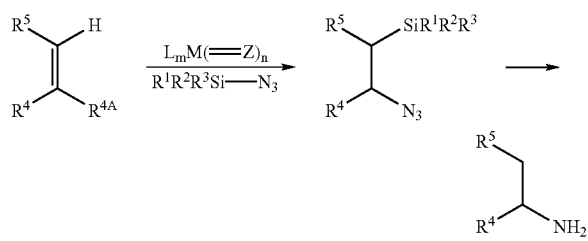

The initial catalytic reaction adding a trialkylsilylazide such as trimethylsilylazide (TMS—$N_3$) provides a β-azidoalkylsilane, which can then undergo protodesilylation and reduction of the azide to the amine. Alternatively, oxidation of the C—Si bond (e.g., via the Tamao-Fleming reaction) followed by reduction of the azide provides a β-amino alcohol:

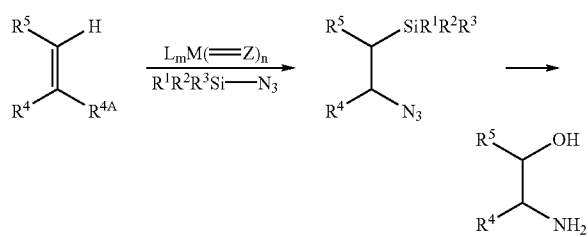

Reaction of an alkyne substrate with a trialkylsilylazide produces a vinyl silane that can be further employed in a cross-coupling reaction, in which reduction of the azide intermediate is followed by hydrolysis of the resultant imine to give a ketone, effectively performing a regioselective hydration of a disubstituted alkyne. This reaction may be illustrated as follows:

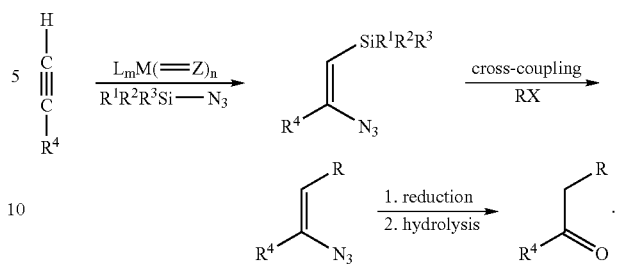

Silylmetalation: The present invention is also useful in the silylmetalation of unsaturated compounds, particularly olefins and carbonyl compounds. The adducts formed upon silylmetalation are useful as intermediates in the further synthesis of a variety of compounds. For example, silylboration of a ketone produces a silyl ether containing a quaternary carbon-boron bond, and subsequent Suzuki cross coupling allows for the introduction of a variety of aryl, vinyl and alkyl halides:

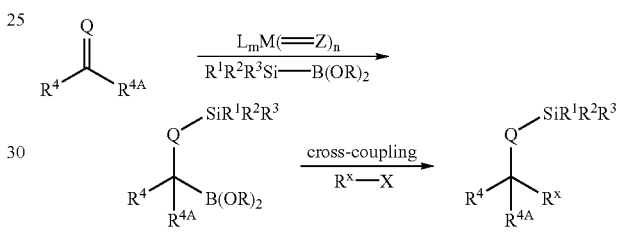

Similarly, silylstannylation produces an alkylstannane that can be further utilized to produce organolithium reagents:

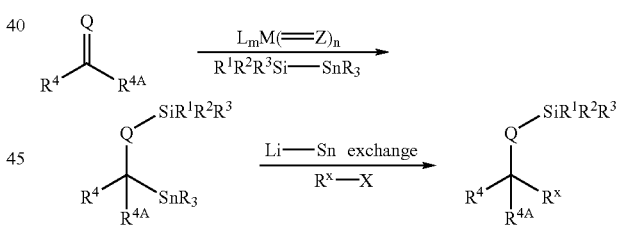

Therefore, the silylmetalation of carbonyl compounds allows for the normal electrophilic behavior of the carbonyl carbon to be reversed, such that this carbon is now reacting with electrophiles. Furthermore, when ketones and 1,1-disubstituted olefins are employed this reaction sequence constitutes a new method for the formation of quaternary centers.

Carbometalation: The addition of silyl cyanides and allyl silanes to carbonyl compounds has been most often accomplished by Lewis acid catalyzed activation of the carbonyl partner (as in the Sakurai reaction). However, the use of Lewis acids excludes the use of substrates that contain Lewis basic functional groups, and the catalysts are often very moisture-sensitive. The complexes and methods of the invention lack these constraints. Furthermore, unlike the Lewis acid catalysts, the present catalysts do not require a Lewis basic carbonyl oxygen to promote the reactions. Therefore, the present invention enables the extension of reactions that have traditionally been limited to addition to the carbonyl to other types of unsaturated substrates. For example, transition metal dioxo catalyzed reaction of trimethylsilyl cyanide with olefins, followed by protodesilylation, produces the equivalent of a Markovnikov hydrocyanation reaction, illustrated in the following scheme:

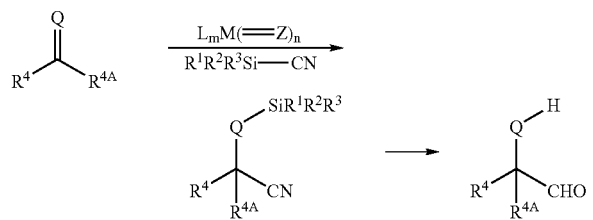

Reduction of the cyano group to the aldehyde affords the equivalent of a hydroformylation reaction in which the regioselectivity of addition has been reversed. When the analogous reaction is carried out employing an alkye, a vinyl silane is obtained:

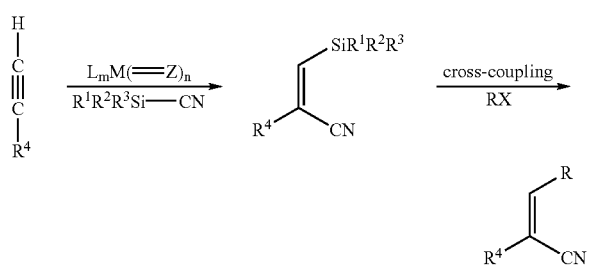

Transition metal catalyzed cross-coupling using the catalysts and methods of the invention thus provides a stereoselective synthetic route to trisubstituted olefins.

Similar reactions can be conducted with allyl silanes in which the activation of the silicon-carbon bond produces a siloxymetal allyl intermediate that can further react with a variety of functional groups. For example, reaction of allyl silanes with olefins, followed by protodesilylation, produces the equivalent of a chemo- and regioselective "ene" reaction:

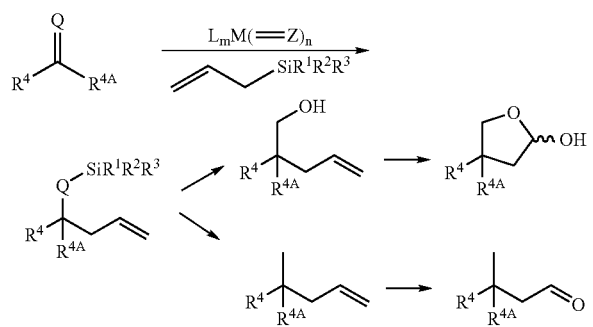

Furthermore, oxidative cleavage of the remaining olefin, as shown above, affords the product which would be derived from a conjugate addition to an α,β-unsaturated aldehyde. Sequential alkyne allylsilylation and cross-coupling provides for regio- and stereoselective entry into 1,4-dienes.

Aldol reactions: The addition of silyl enol ethers to aldehydes (Mukaiyama aldol) has previously been catalyzed by either Lewis acid catalyzed activation of the aldehyde (Sawamura et al., in *Catalytic Asymmetric Synthesis* $2^{nd}$ ed., Ojima, Ed., Wiley-VCH, New York, 2000, Chapter 8B1; Carreira, in *Catalytic Asymmetric Synthesis* $2^{nd}$ ed., Ojima, Ed., Wiley-VCH, New York, 2000, Chapter 8B), transition metal catalyzed activation of the enol ether (Krüiger et al. (1998) *J. Am. Chem. Soc.* 120:837; Sodeoka et al. (1995) *J. Org. Chem.* 60:2648), or Lewis base catalyzed activation of trichlorosilylenol ethers (Denmark (2000) *Acc. Chem. Res.* 33:432). These methods suffer from air and moisture sensitivity as well as functional group incompatibility. The present methodology overcomes these limitations in the art by employing air- and moisture-insensitive transition metal complexes as catalysts that are also tolerant of most functional groups. The following scheme illustrates such a reaction in which a transition metal complex of the invention activates the Si—O bond of a silyl enol ether to afford novel metal enolates:

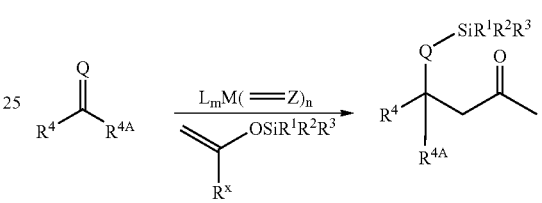

Coordination of aldehydes, ketones and imines to the metal center promotes the addition of these enolates. Therefore, in these aldol reactions the transition metal complex serves as a bifunctional catalyst to activate both the enolate and the electrophile. The methodology readily extends to the three-component coupling of a silane, an enone and an aldehyde, providing a new route to aldol adducts. The hydrosilylation of an enone produces a metal enolate that can subsequently undergo reaction with aldehydes, ketones and imines:

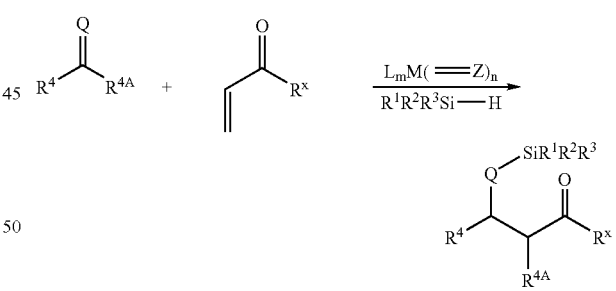

Hydro- and carbometalation initiated cyclization/polymerization: The transition metal complexes provided herein additionally serve as well-defined and tunable catalysts for olefin polymerizations, illustrated in the following schemes:

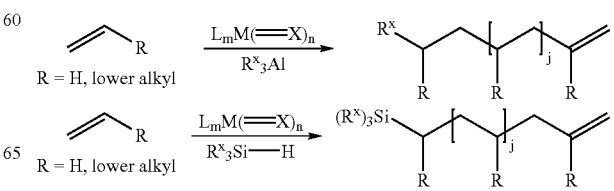

Without wishing to be bound by theory, it is proposed that the addition of a trialkyl metal complex such as trimethylaluminum to a transition metal-dioxo complex will form an aluminoxymetal alkyl, such that coordination of the olefin to the metal center precedes insertion of the olefin into the metal-carbon bond. Furthermore, coordination of a second equivalent of organoaluminum to the remaining oxo-ligand, which would decrease the π-donation from the oxo to the metal, further facilitates the insertion reaction. Alternatively, olefin polymerization may be initiated by the previously discussed hydrosilylation reaction. The principles applied in the polymerization reactions may also be applied in cyclization reactions. The cyclization reaction may be initiated by a number of the reactions that have previously been discussed. For example, hydro-, azido-, boryl- or cyano-metalation of an alkyne or olefin produces an alkyl metal intermediate. Insertion of pendant unsaturation (e.g. an aldehyde, imine or olefin) into the alkylmetal bond followed by silyl transfer produces the cyclized products, illustrated as follows:

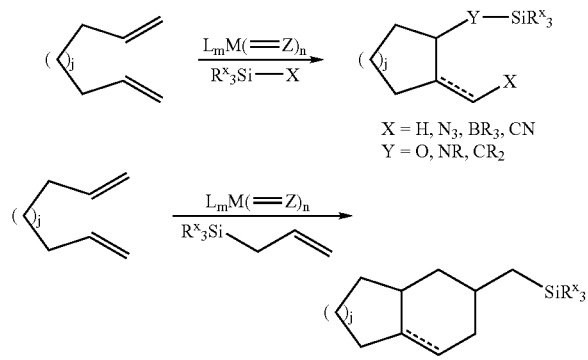

In allylmetalation, the alkylmetal intermediate generated from the first cyclization reaction can undergo further reaction with the allyl moiety to provide bicyclic products. This represents a novel utility for allylsilanes in which they serve as one of the partners in a [2+2+2] cycloaddition reaction.

Epoxide/aziridine opening: Epoxides are some of the most versatile building blocks in organic synthesis. As such, methods for enantioselective additions of nucleophiles, including water, to epoxides are highly desirable. The present invention encompasses such reactions, wherein nucleophilic reactants are activated by the oxo (or sulfido or amido) moiety of a transition metal complex as provided herein, and the epoxide or aziridine ring is activated by coordination to the Lewis acid metal center.

It will be appreciated that the foregoing reactions are merely illustrative of the many types of nucleophilic addition reactions enabled by the present catalytic method, and the invention is not limited with respect to the specifically exemplified reactions above.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental:

All aldehydes, ketones, imines, olefins and silanes (triethylsilane, dimethylphenylsilane, t-butyldimethyl silane, trimethylsilylcyanide and the silyl enol ethers) were purchased from Aldrich and used without further purification. The bis-oxazoline ligands were purchased from Aldrich (Milwaukee, Wis.), the bis-phosphine ligands were purchased from Strem Chemicals Inc. (Newburyport, Mass.), and the oxazolylphenol ligands were prepared from 2-cyanophenol (Bolm et al. (1991) *Chem. Ber.* 124:1173). Iodo[bis(triphenylphosphine)] dioxorhenium(V) was prepared from potassium perrhenate by a modification of Ciani et al. (1983) *Inorg. Chim. Acta.* 72:29, bis(triphenylarsine)oxorhenium(V)trichloride was prepared according to Fonatine et al. (1991) *J. Chem. Soc., Dalton Trans,* 1519, and bis(triphenylphosphine) oxorhenium(V)trichloride was prepared according to Chatt et al. (1962) *J. Chem. Soc.,* 4019. Unless otherwise specified, all other reagents were also purchased from commercial suppliers and used without further purification. All solvents were purified by passage through a solvent column (containing activated A-2 alumina; see Pangbom et al. (1996) *Organometallics* 15:1518-1520.). Analytical thin-layer chromatography (TLC) was performed using silica gel 60 F254 precoated plates (0.25 mm thickness) with a fluorescent indicator. Flash column chromatography was performed using silica gel 60 (230-400 mesh) from EM Science. $^{1}H$, $^{13}C$, and $^{31}P$ NMR spectra were obtained on a Varian 300 MHz Fourier Transform spectrometer (300 MHz $^{1}H$, 75.4 MHz $^{13}C$, 121.4 MHz $^{31}P$). All chemical shift values are given in parts-per million (δ) and are referenced with respect to residual solvent ($^{1}H$ and $^{13}C$) or phosphoric acid ($^{31}P$).

EXAMPLE 1

General Procedure for Reduction of Aldehydes and Ketones

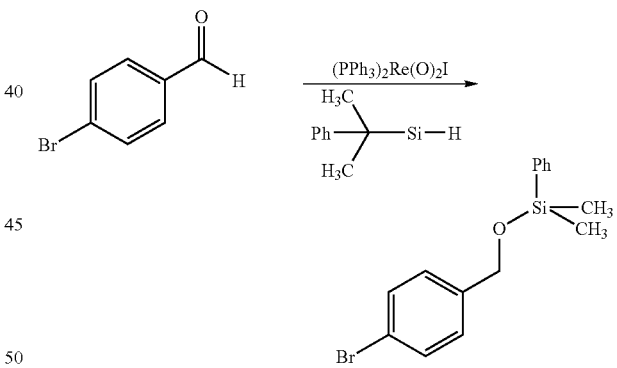

In a 5 mL flask opened to the air, to a clear solution of 4-bromobenzaldehyde (91 mg, 0.492 mmol) in benzene (0.5 mL) was added dimethylphenylsilane (Me$_{2}$PhSiH) (91 μL, 0.590 mmol). The flask was placed in a 60° C. bath and iodo[bis(triphenylphosphine)]dioxorhenium(V) (9 mg, 0.010 mmol) was added. The resulting brown solution was heated at 60° C. for 2 hours. The crude reaction mixture was directly applied to a SiO$_{2}$ column and chromatographed eluting with 99:1 hexanes:diethyl ether to afford dimethylphenylsilyl protected 4-bromobenzylalcohol (145 mg, 92% yield) as a colorless liquid.

The reaction was repeated using different aldehydes and silanes, including triethylsilane (Et$_{3}$SiH), t-butyldimethylsilane (t-BuMe$_{2}$SiH), and triisopropylsilane ((i-Pr)$_{3}$SiH). The reaction conditions, mole % catalyst, and isolated yield are indicated in Table 1.

TABLE 1

Rhenium(V) catalyzed hydrosilation of aldehydes

| aldehyde | silane | mol % (PPh$_3$)$_2$Re(O)$_2$I | time/temp. | isolated yield |
|---|---|---|---|---|
| X = CH$_3$O 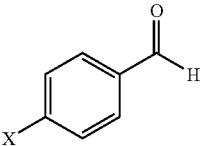 | Et$_3$SiH | 5% | 15 min./60° | 91% |
|  | Et$_3$SiH | 5% | 2 h/60° | 95% |
|  | Et$_3$SiH | 2% | 18 h/rt | 93% |
|  | Me$_2$PhSiH | 2% | 2 h/rt | 94% |
|  | t-BuMe$_2$SiH | 5% | 2 h/60° | 89% |
|  | (i-Pr)$_3$SiH | 5% | 3 h/60° | 0% |
| = (CH$_3$)$_2$N | Me$_2$PhSiH | 5% | 30 min./60° | 86% |
| = H | Me$_2$PhSiH | 2% | 2 h/60° | 94% |
| = Br | Me$_2$PhSiH | 2% | 2 h/60° | 92% |
| = NO$_2$ | Me$_2$PhSiH | 2% | 2 h/60° | 90% |
| 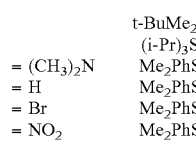 | Et$_3$SiH | 2% | 2 h/60° | 95% |
| 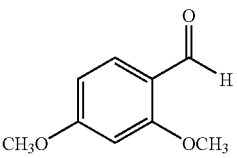 | Et$_3$SiH | 1% | 2 h/60° | 83% |
| 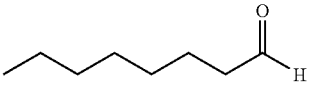 | Et$_3$SiH | 1% | 2 h/60° | 57%(30%)[a] |
|  | Me$_2$PhSiH | 1% | 2 h/60° | 69%(24%) |
| 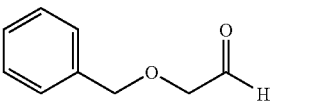 | Me$_2$PhSiH | 1% | 2 h/60° | 87%(5%)[a] |

[a]Isolated yield of alcohol in parenthesis

The reaction was then carried out using additional electrophilic reactants, including a variety of ketones, and, as nucleophiles, the silanes Et$_3$SiH and Me$_2$PhSiH. The reaction conditions, mole % catalyst, and isolated yield are indicated in Table 2.

TABLE 2

Rhenium(V) catalyzed hydrosilation of ketones

| Aldehyde | silane | catalyst[a] | time/temp. | isolated yield |
|---|---|---|---|---|
| 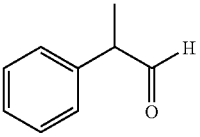 X = H<br>= CN | Et$_3$SiH<br>Me$_2$PhSiH | 5% A<br>5% A | 6 h/80°<br>14 h/80° | 79%<br>82% |
| 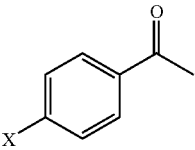 | Me$_2$PhSiH | 5% A | 5 h/60° | 63%(6%)[b] |

TABLE 2-continued

Rhenium(V) catalyzed hydrosilation of ketones

| Aldehyde | silane | catalyst[a] | time/temp. | isolated yield |
|---|---|---|---|---|
| 4-tert-butylcyclohexanone | $Me_2PhSiH$ | 5% A | 8 h/80° | 81% (9:1 trans:cis) |
| 4,4'-bis(trifluoromethyl)benzophenone-type (bis-CF3 aryl ketone) | $Me_2PhSiH$ | 5% A | 14 h/80° | 21%(60%)[b] |
| X = H; = CH₃ (α-substituted ethyl ketone) | $Me_2PhSiH$ $Me_2PhSiH$ | 5% A 5% A | 5 h/80° 5 h/80° | 57% 0% |
| 2-methyl-1-tetralone | $Me_2PhSiH$ $Me_2PhSiH$ | 5% A 5% B | 10 h/80° 10 h/80° | 0% 0% (38%)[b] (3:2:1 trans:cis) |
| Hajos–Parrish diketone analog | $Me_2PhSiH$ | 5% A | 4 h/80° | 73% (1:1:1 dr) |

[a]Catalyst: A $(PPh_3)_2Re(O)_2I$ B $(PPh_3)_2Re(O)Cl_3$
[b]isolated yield of alcohol in parenthesis

EXAMPLE 2

General Procedure for Reduction of Imines

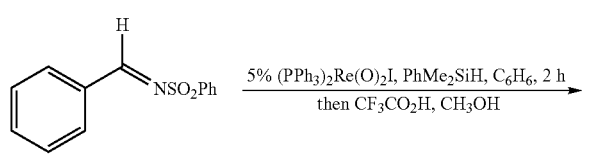

In a 5 mL flask opened to the air, to a clear solution of N-benzylidenebenzene sulfonamide (100 mg, 0.408 mmol) in benzene (0.4 mL) was added dimethylphenylsilane (125 µL, 0.816 mmol). The flask was placed in a 60° C. bath and iodo[bis(triphenylphosphine)] oxorhenium(V) (18 mg, 0.021 mmol) was added. The resulting brown solution was heated at 60° C. for 2 hours. To the reaction mixture was added methanol (0.4 mL) followed by trifluoroacetic acid (35 µL), and heating continued for an additional 2 h. The crude reaction mixture was directly applied to a $SiO_2$ column and chromatographed eluting with 1:1 hexanes: diethyl ether to afford N-phenylsulfonylbenzylamine (87 mg, 86% yield) as a slightly yellow solid.

EXAMPLE 3

General Procedure for Hydrogenation of Olefins

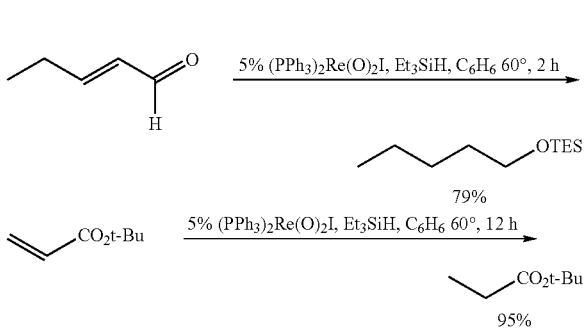

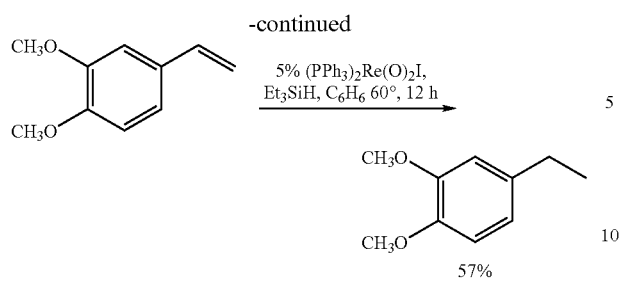

In a 5 mL flask opened to the air, to a clear solution of 3,4-dimethoxystyrene (100 µL, 0.755 mmol) in benzene (0.8 mL) was added triethylsilane (240 µL, 0.816 mmol). The flask was placed in a 60° C. bath and iodo[bis(triphenylphosphine)]dioxorhenium(V) (32 mg, 0.037 mmol) was added. The resulting brown solution was heated at 60° C. for 12 hours. The crude reaction mixture was directly applied to a SiO$_2$ column and chromatographed eluting with 4:1 hexanes:diethyl ether to afford 3,4-dimethoxyethylbenzene (52 mg, 57% yield) as a colorless liquid. The reaction was repeated using pent-2-enal and t-butyl acrylate as the electrophilic reactants, as indicated in the first two schemes above (wherein "TES" represents triethylsilyl).

EXAMPLE 4

Representative Procedure for Synthesis of Rhenium (V) Dioxo Complexes

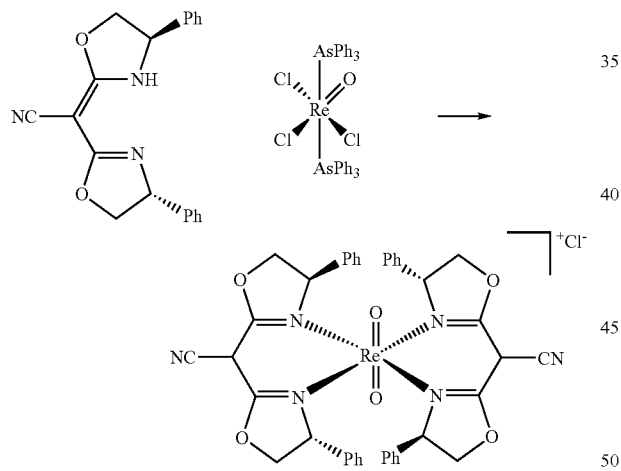

To a yellow suspension of bis(triphenylarsine)oxorhenium(V) trichloride (2.7 g, 2.93 mmol) in methylene chloride (60 mL) was added (4S)-(+)-phenyl-α-[(4S)-phenyloxazolin-2-oxazoline-2-acetonitrile (1.0 g, 3.02 mmol). The resulting brown/green reaction mixture was stirred at room temperature for 1 h, then diluted with diethyl ether (150 mL). The precipitated green solid was collected and washed with diethyl ether (3×50 mL) to afford the desired complex (1.82 g, 68%) as a grass green solid. $^1$H-NMR (CD$_2$Cl$_2$): δ 7.42 (m 20H), 5.56 (br s, 4H), 5.23 (br t, 4H), 4.68 (br t, 4H). MS: 915.1034 and 917.0946 (M$^+$Cl$^-$), 879.1611 and 881.1560 (M).

An analogous procedure was carried out to prepare the following complexes from bis(triphenylarsine)oxorhenium(V)trichloride and an appropriately substituted 2-oxazolidin-2-ylidenemethyl-4,5-dihydrooxazole:

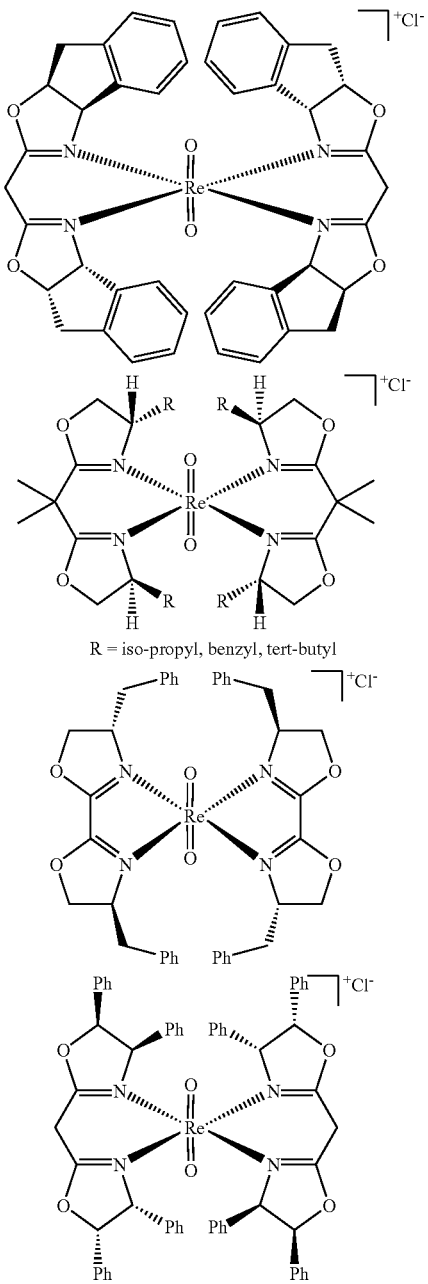

EXAMPLE 5

Representative Procedure for Synthesis of Rhenium (V) Phenoxy-Oxazolidine Complexes

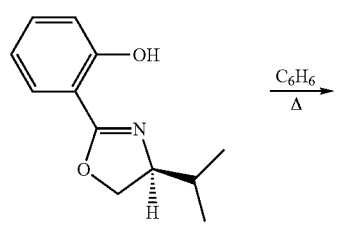

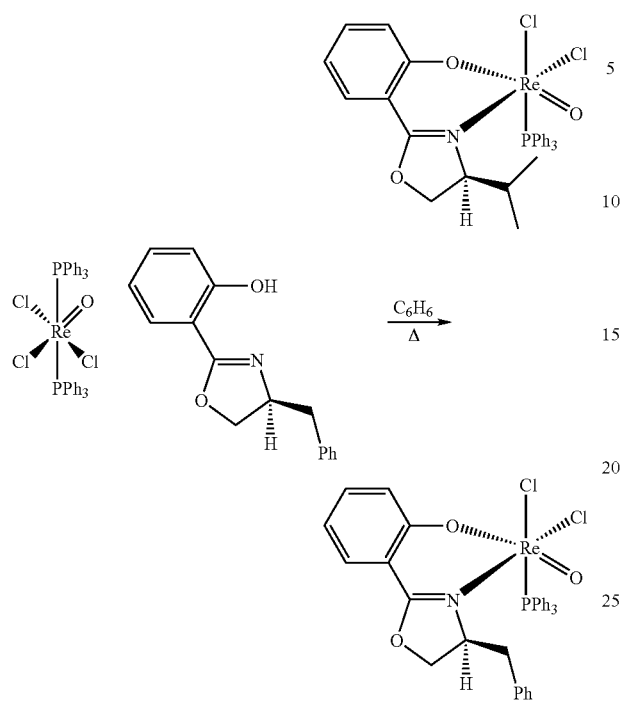

To a clear solution of the 2-(2-hydroxyphenyl)-(4S)-isopropyloxazolidine (3.7 g, 18.0 mmol) in benzene (150 mL), at reflux, was added bis(triphenylphosphine) oxorhenium(V) trichloride (1.5 g, 1.80 mmol). The resulting green solution was refluxed for 2 h, cooled to room temperature and concentrated to approximately 50 mL. The green precipitate was collected and washed with diethyl ether (3×50 mL), to afford the chiral rhenium complex (1.10 g, 83%) as a green solid. $^1$H-NMR (CD$_2$Cl$_2$): δ 7.60–7.37 (m, 19H), 7.12 (ddq, J=8.2, 7.1 and 1.8 Hz, 1H), 6.91 (td, J=7.1 and 1.8 Hz, 1H), 6.63 (dd, J=8.2 and 0.8 Hz), 4.48 (dd, J=9.8 and 4.3 Hz, 1H), 3.96 (t, J=9.8 Hz, 1H), 3.57 (ddd, J=9.8, 4.0 and 2.8 Hz, 1H), 2.92 (m, 1H), 1.00 (d, J=6.6 Hz, 3H), 0.82 (d, J=7.1 Hz, 3H). $^{31}$P-NMR (CD$_2$Cl$_2$): −18.5. An analogous procedure was carried out to synthesize the benzyloxazolidine analogue using 2-(2-hydroxyphenyl)-(4S)-benzyloxazolidine as a starting material.

EXAMPLE 6

Representative Procedure for Synthesis of Chiral Bisphosphine Rhenium (V) Complexes

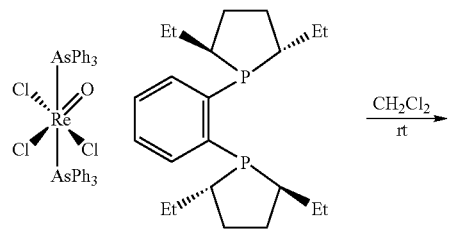

To a yellow suspension of bis(triphenylarsine)oxorhenium(V) trichloride (1.3 g, 1.41 mmol) in methylene chloride (40 mL) was added 1,2-bis((2S,5S)-2,5-diethylphospholano) benzene ((S,S)-Et-DUPHOS, obtained from Strem Chemicals Inc., Newburyport, Mass.) (500 mg, 1.38 mmol), as shown in the first scheme above. The resulting green reaction mixture was stirred at room temperature for 10 h, then filtered to remove some white precipitate. The filtrate was concentrated to approximately 10 mL and then diluted with diethyl ether (150 mL). The precipitated green solid was collected and washed with diethyl ether (3×50 mL) to afford the desired complex (1.08 g, 81%) as a green solid. $^1$H-NMR (CD$_2$Cl$_2$): δ 8.0 (m, 2H), 7.8 (m, 2H), 3.0-2.0 (m, 8H), 2.0-1.0 (m, 24H). $^{31}$P-NMR (CD$_2$Cl$_2$): 40.20, 31.73. An analogous procedure was used to prepare the rhenium complex shown in the second scheme above, substituting 2,2'-bis(diphenylphosphino)-1,1'-binaphthyl (BINAP) for ((S,S)-Et-DUPHOS.

EXAMPLE 7

General Procedure for Enantioselective Reduction of Aldehydes and Ketones

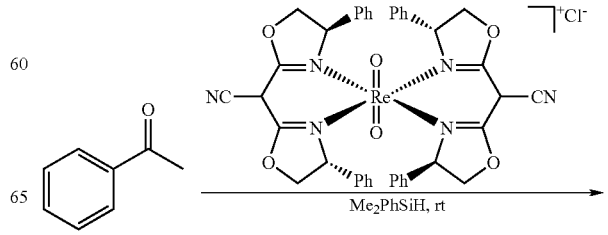

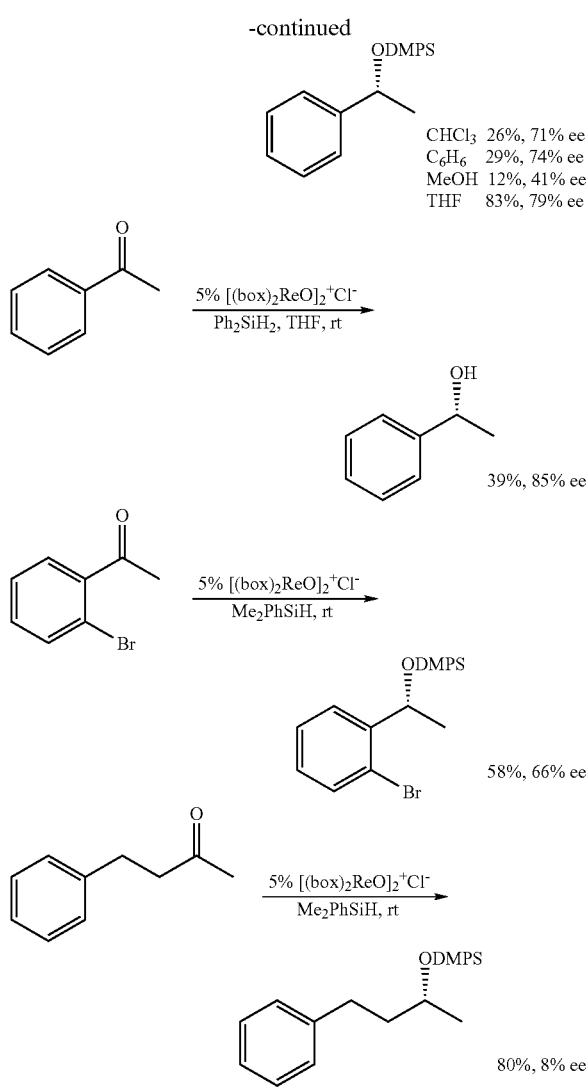

In a 5 mL flask opened to the air, to a clear solution of acetophenone (100 mg, 0.832 mmol) in tetrahydrofuran (0.8 mL) was added dimethylphenylsilane (91 μL, 0.590 mmol) followed by the chiral dioxorhenium(V) complex (25 mg, 0.042 mmol). The resulting brown solution was heated at room temperature for 18 hours. The crude reaction mixture was directly applied to a SiO$_2$ column and chromatographed eluting with 98:2 hexanes:diethyl ether to afford dimethylphenylsilyl protected 4-bromobenzylalcohol (176 mg, 83% yield) as a colorless liquid. $^1$H-NMR (C$_6$D$_6$): δ 7.54 (m, 2H), 7.25–7.02 (m, 8H), 4.74 (q, J=6.3 Hz, 1H), 1.33 (d, J=6.3 Hz, 3H), 0.27 (s, 3H), 0.21 (s, 3H). $^{13}$C-NMR (C$_6$D$_6$): δ 146.7, 138.4, 133.9, 129.8, 128.5, 128.1, 127.2, 125.7, 71.6, 27.4, −0.5, −1.0.

The reaction was repeated using: (a) acetophenone and diphenylsilane; (b) 2-bromoacetophenone and dimethylphenylsilane; and (c) 4-phenyl-butan-2-one and dimethylphenylsilane, as indicated in the above schemes. Enantiomeric excess ("ee") was determined by deprotection of the silyl ether with tetrabutylammonium fluoride (TBAF) to afford the alcohol. Enantiomers of the alcohol were separated by gas chromatography using a chiral (G-TA) column. Retention times: minor enantiomer 24.83 min.; major enantiomer 24.98 min.

We claim:

1. A method for catalyzing a hydrosilylation reaction, comprising contacting (a) an electrophilic reactant containing an electrophilic site in the form of an unsaturated bond between a carbon atom and a second atom Q, wherein Q is selected from O, S, N and C, with (b) a silane having the structure of formula (I)

wherein: R$^1$, R$^2$ and R$^3$ are independently selected from the group consisting of hydrocarbyl, substituted hydrocarbyl, heteroatom-containing hydrocarbyl, and substituted heteroatom-containing hydrocarbyl and X is hydrogen, cyano, cyanato, azido, alkenyl, alkenyloxy, alkenylthio, or boronato, in the presence of (c) a catalytically effective amount of a transition metal oxo, sulfido or amido complex, wherein: (i) the transition metal of the complex is selected from Groups 6, 7, and 8 of the Periodic Table of the Elements; and (ii) the transition metal complex has the structure L$_m$M(=Z)$_n$ wherein: m is an integer in the range of 2 to 5 inclusive; n is 1 or 2; the L groups are ligands, and may be the same or different; M is the transition metal; and Z is O, S or NR$^1$ wherein R$^1$ is hydrogen or hydrocarbyl, under reaction conditions that provide for nucleophilic addition of the silane to the electrophilic site of the electrophilic reactant.

2. The method of claim 1, wherein M is Mo, W, Re, Ru or Os.

3. The method of claim 2, wherein Z is O.

4. The method of claim 1, wherein the complex is charged and associated with a counterion of opposite charge.

5. The method of claim 3, wherein m is 5, n is 1, M is Re, and the L groups are monodentate ligands.

6. The method of claim 3, wherein m is 4, n is 1, M is Re, one L group is a bidentate ligand, and three L groups are monodentate ligands.

7. The method of claim 3, wherein m is 2, n is 2, M is Re, the L groups are bidentate ligands, and the complex is positively charged and associated with an anionic counterion.

8. The method of claim 1, wherein R$^1$, R$^2$ and R$^3$ are independently selected from the group consisting of C$_1$-C$_{20}$ alkyl and C$_5$-C$_{20}$ aryl.

9. The method of claim 8, wherein X is hydrogen, cyano, alkenyl, alkenyloxy, or boronato.

10. The method of claim 1, wherein the electrophilic reactant has the structure of formula (II)

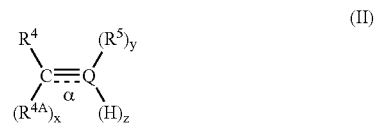

wherein:

R$^1$, R$^{4A}$ and R$^5$ are independently selected from the group consisting of hydrogen, hydrocarbyl, substituted hydrocarbyl, heteroatom-containing hydrocarbyl, substituted heteroatom-containing hydrocarbyl, and a functional group;

α is an optional bond; and x, y, and z are zero or 1, with the provisos that (a) when Q is O or S, then α is absent, x is 1, and y and z are zero; (b) when Q is N, then α is absent, x and z are 1, and y is zero; (c) when Q is C and a is absent, then x, y and z are 1; and (d) when Q is C and α is present, then x and y are zero and z is 1.

11. The method of claim 10, wherein α is absent, such that the electrophilic reactant has the structure of formula (III)

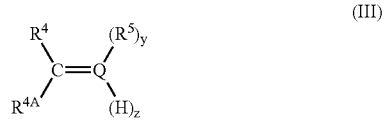

(III)

and nucleophilic addition of the silane reactant results in a reaction product having the structure of formula (IV)

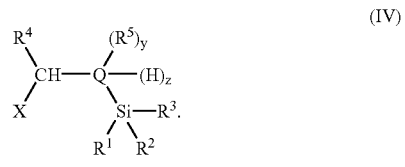

(IV)

12. The method of claim 1, wherein the transition metal complex has the structure of formula (V)

(V)

wherein M is a Group 7 transition metal, $L^1$ and $L^2$ are neutral electron donor ligands, and $R^6$, $R^7$ and $R^8$ are anionic ligands, or $R^7$ and $R^8$ taken together form a second oxo moiety.

13. The method of claim 12, wherein:
M is Re;
$L^1$ and $L^2$ are independently selected from the group consisting of phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether; and
$R^6$, $R^7$ and $R^8$ are independently selected from the group consisting of hydrogen, halide, $C_1$-$C_{20}$ alkyl, $C_5$-$C_{20}$ aryl, $C_1$-$C_{20}$ alkoxy, $C_5$-$C_{20}$ aryloxy, $C_3$-$C_{20}$alkyldiketonate, $C_5$-$C_{20}$ aryldiketonate, $C_2$-$C_{20}$ alkoxycarbonyl, $C_5$-$C_{20}$ aryloxycarbonyl, $C_2$-$C_{20}$ acyl, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of halide, are optionally further substituted with one or more groups selected from halide, $C_1$-$C_6$ alkyl, $C_1$-$C_{6\ 8}$ alkoxy, and phenyl, or $R^7$ and $R^8$ taken together form a second oxo moiety.

14. The method of claim 13, wherein:
$L^1$ and $L^2$ are independently selected from phosphines of the formula $PR_3$, where each R is independently aryl or $C_1$-$C_{10}$ alkyl; and
$R^1$, $R^7$ and $R^8$ are independently selected from the group consisting of halide and lower alkoxy, or $R^7$ and $R^8$ taken together form a second oxo moiety.

15. The method of claim 14, wherein:
$L^1$ and $L^2$ are independently selected from the group consisting of —P(cyclohexyl)$_3$, —P(cyclopentyl)$_3$, —P(isopropyl)$_3$, —P(phenyl)$_3$, P(phenyl)$_3$, —P(phenyl)$_2$($R^9$) and —P(phenyl)($R^9$)$_2$, in which $R^9$ is lower alkyl; and
$R^6$, $R^7$ and $R^8$ are independently selected from the group consisting of halide, methoxy, ethoxy, or $R^7$ and $R^8$ taken together form a second oxo moiety.

16. The method of claim 15, wherein $R^7$ and $R^8$ together form a second oxo moiety.

17. The method of claim 16, wherein $L^1$ and $L^2$ are —P(cyclohexyl)$_3$ or —P(cyclopentyl)$_3$.

18. The method of claim 17, wherein $R^6$ is halide.

19. The method of claim 15, wherein $R^6$ $R^7$ and $R^8$ are independently selected from the group consisting of halide, methoxy and ethoxy.

20. The method of claim 19, wherein $R^6$ is ethoxy or halide and $R^7$ and $R^8$ are halide.

21. The method of claim 1, wherein the transition metal complex has the structure of formula (VI)

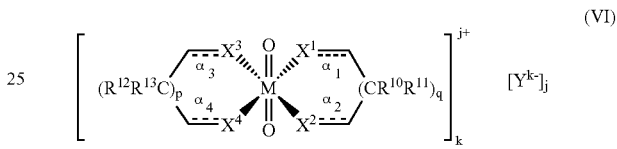

(VI)

wherein:
M is a Group 7 or Group 8 transition metal;
$Y^{-k}$ is an anion bearing a charge of –k;
either j and k are both 1, or j and k are both 2;
p and q are independently zero or 1;
$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups;
$α_1$, $α_2$, $α_3$ and $α_4$ are optional bonds;
$X^1$, $X^2$, $X^3$ and $X^4$ are independently selected from $NR^{14}$, $NR^{15} R^{16}$ and $PR^{17} R^{18}$, with the proviso that when any of $X^1$, $X^2$, $X^3$ and $X^4$ are $NR^{14}$, then the adjacent $α_1$, $α_2$, $α_3$ or $α_4$ is present, and when any of $X^1$, $X^2$, $X^3$ and $X^4$ are $NR^{15} R^{16}$ or $PR^{17} R^{18}$, then the adjacent $α_1$, $α_2$, $α_3$ or $α_4$ is absent; and
$R^{14}$, $R^{15}$, $R^{16}$, $R^{17}$ and $R^{18}$ are independently selected from the group consisting of hydrocarbyl, substituted hydrocarbyl, heteroatom-containing hydrocarbyl, and substituted heteroatom-containing hydrocarbyl, and further wherein any two or more of $R^{14}$, $R^{15}$, $R^{16}$, $R^{17}$ and $R^{18}$ may be taken together to form a cyclic group.

22. The method of claim 21, wherein the transition metal complex has the structure of formula (VII)

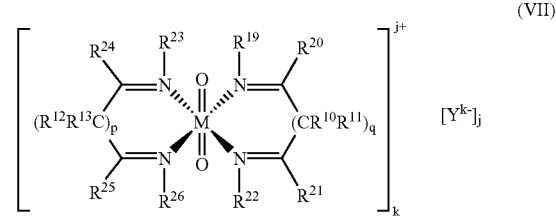

(VII)

wherein:
$R^{19}$, $R^{22}$, $R^{23}$ and $R^{26}$ are independently selected from the group consisting of hydrocarbyl, substituted hydrocarbyl, heteroatom-containing hydrocarbyl, and substituted heteroatom-containing hydrocarbyl; and $R^{20}$, $R^{21}$, $R^{24}$ and $R^{25}$ are independently selected from the group consisting of hydrogen, hydrocarbyl, substituted hydrocarbyl, heteroatom-containing hydrocarbyl, and substituted heteroatom-containing hydrocarbyl, and further wherein any two or more of $R^{19}$, $R^{20}$, $R^{21}$, $R^{22}$, $R^{23}$, $R^{24}$, $R^{25}$ and $R^{26}$ may be taken together to form a cyclic group.

23. The method of claim 22, wherein M is Re, and j and k are 1.

24. The method of claim 22, wherein M is Os or Ru, and j and k are 2.

25. The method of claim 22, wherein $R^{19}$ and $R^{20}$, $R^{21}$ and $R^{22}$, $R^{23}$ and $R^{24}$, and $R^{25}$ and $R^{26}$ are linked to form cyclic groups, such that the transition metal complex has the structure of formula (VIII)

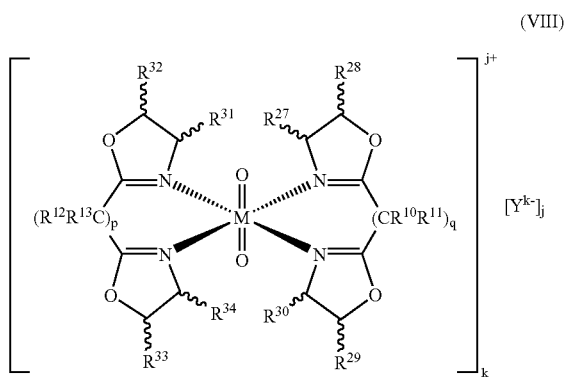

(VIII)

wherein $R^{27}$, $R^{28}$, $R^{29}$, $R^{30}$, $R^{31}$, $R^{32}$, $R^{33}$ and $R^{34}$ are independently selected from the group consisting of hydrogen, $C_1$-$C_{12}$ alkyl, phenyl, and benzyl, or wherein $R^{27}$ and $R^{28}$, $R^{29}$ and $R^{30}$, $R^{31}$ and $R^{32}$, and/or $R^{33}$ and $R^{34}$ are linked to form a cyclic group.

26. The method of claim 22, wherein M is Re, and j and k are 1.

27. The method of claim 23, wherein M is Os or Ru, and j and k are 2.

28. The method of claim 25, wherein the complex has the structure of formula (VIIIA)

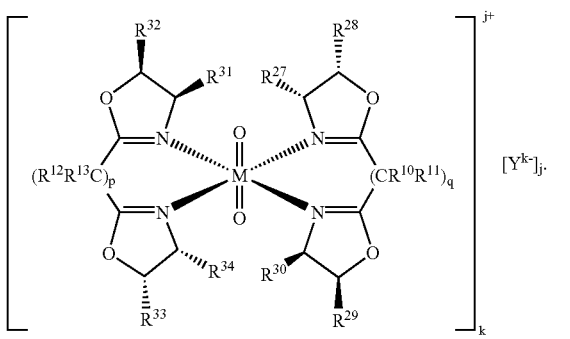

(VIIIA)

29. The method of claim 28, wherein M is Re, and j and k are 1.

30. The method of claim 29, wherein M is Os or Ru, and j and k are 2.

31. The method of claim 1, wherein the transition metal complex has the structure of formula (VIIIB)

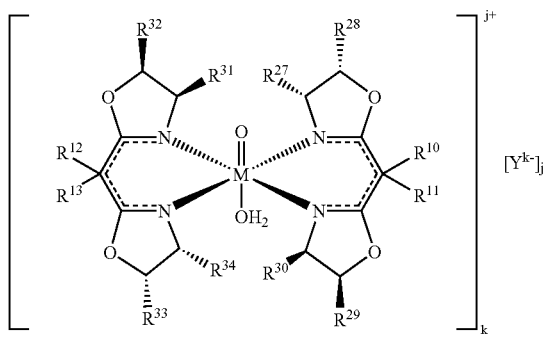

(VIIIB)

wherein:
M is a Group 7 or Group 8 transition metal;
$Y^{-k}$ is an anion bearing a charge of -k;
either j and k are both 1, or j and k are both 2;
p and q are independently zero or 1;
$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups; and
$R^{27}$, $R^{28}$, $R^{29}$, $R^{30}$, $R^{31}$, $R^{32}$, $R^{33}$ and $R^{34}$ are independently selected from the group consisting of hydrogen, $C_1$-$C_{12}$ alkyl, phenyl, and benzyl, or wherein $R^{27}$ and $R^{28}$, $R^{29}$ and $R^{30}$, $R^{31}$ and $R^{32}$, and/or $R^{33}$ and $R^{34}$ are linked to form a cyclic group.

32. The method of claim 21, wherein the complex has the structure of formula (IX)

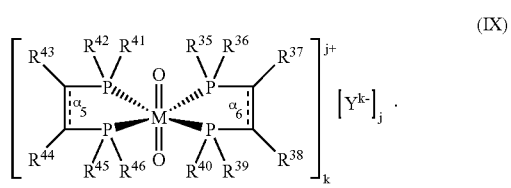

(IX)

wherein:
$\alpha_5$ and $\alpha_6$ are optional bonds;
$R^{35}$, $R^{36}$, $R^{39}$, $R^{40}$, $R^{41}$, $R^{42}$, $R^{45}$ and $R^{46}$ are independently selected from the group consisting of hydrocarbyl, substituted hydrocarbyl, heteroatom-containing hydrocarbyl, and substituted heteroatom-containing hydrocarbyl; and
$R^{37}$, $R^{38}$, $R^{43}$ and $R^{44}$ are independently selected from the group consisting of hydrogen, hydrocarbyl, substituted hydrocarbyl, heteroatom-containing hydrocarbyl, and substituted heteroatom-containing hydrocarbyl,
and further wherein any two or more of $R^{35}$, $R^{36}$, $R^{37}$, $R^{38}$ $R^{39}$, $R^{40}$, $R^{41}$, $R^{42}$, $R^{43}$, $R^{44}$ and $R^{45}$ may be taken together to form a cyclic group.

33. The method of claim 32, wherein M is Re, and j and k are 1.

34. The method of claim 33, wherein M is Os or Ru, and j and k are 2.

35. The method of claim 32, wherein $\alpha_5$ and $\alpha_6$ are absent.

36. The method of claim 35, wherein $R^{37}$, $R^{38}$, $R^{43}$ and $R^{44}$ are hydrogen.

37. The method of claim 36, wherein $R^{35}$, $R^{36}$, $R^{39}$, $R^{40}$, $R^{41}$, $R^{42}$, $R^{45}$ and $R^{46}$ are aryl.

38. The method of claim 37, wherein $R^{35}$, $R^{36}$, $R^{39}$, $R^{40}$, $R^{41}$, $R^{42}$, $R^{45}$ and $R^{46}$ are phenyl.

39. The method of claim 32, wherein $\alpha_5$ and $\alpha_6$ are present.

40. The method of claim 39, wherein $R^{37}$ and $R^{38}$ taken together, and $R^{43}$ and $R^{44}$ taken together, are phenyl or naphthalenyl.

41. The method of claim 1, wherein the transition metal complex has the structure of formula (X)

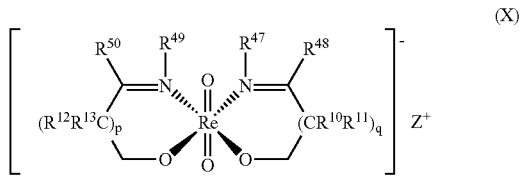

(X)

wherein:

$Z^+$ is a cation;

p and q are independently zero or 1;

$R^{10}$, $R^{11}$, $R^{12}$ and $R^{13}$ are independently selected from the group consisting of hydrogen, hydrocarbyl, substituted hydrocarbyl, heteroatom-containing hydrocarbyl, substituted heteroatom-containing hydrocarbyl, and functional groups;

$R^{47}$ and $R^{48}$ are independently selected from the group consisting of hydrocarbyl, substituted hydrocarbyl, heteroatom-containing hydrocarbyl, and substituted heteroatom-containing hydrocarbyl; and $R^{49}$ and $R^{50}$ are independently selected from the group consisting of hydrogen, hydrocarbyl, substituted hydrocarbyl, heteroatom-containing hydrocarbyl, and substituted heteroatom-containing hydrocarbyl, and further wherein either $R^{47}$ and $R^{49}$, or $R^{47}$ and $R^{48}$ an/or $R^{49}$ and $R^{50}$, may be taken together to form a cyclic group.

42. The method of claim 1, wherein the transition metal complex has the structure of formula (XI)

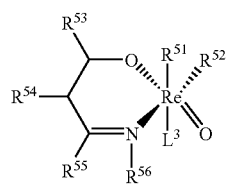

(XI)

wherein:

$L^3$ is a neutral electron donor ligand;

$R^{51}$ and $R^{52}$ are anionic ligands;

$R^{53}$, $R^{54}$ and $R^{55}$ are independently selected from the group consisting of hydrogen, hydrocarbyl, substituted hydrocarbyl, heteroatom-containing hydrocarbyl, and substituted heteroatom-containing hydrocarbyl; and $R^{56}$ is selected from the group consisting of hydrocarbyl, substituted hydrocarbyl, heteroatom-containing hydrocarbyl, and substituted heteroatom-containing hydrocarbyl, and further wherein $R^{53}$ and $R^{54}$, and/or $R^{55}$ and $R^{56}$, may be taken together to form a cyclic group.

43. The method of claim 42, wherein the transition metal complex has the structure of formula (XII)

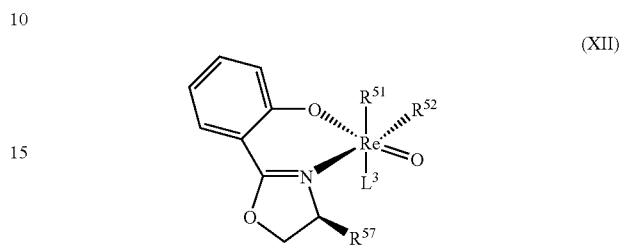

(XII)

wherein:

$L^3$ is P(cyclohexyl)$_3$ or —P(cyclopentyl)$_3$;

$R^{51}$ and $R^{52}$ are halide; and $R^{57}$ is selected from the group consisting of hydrogen, $C_1$-$C_{12}$ alkyl, phenyl, and benzyl.

44. The method of claim 1, wherein the transition metal complex has the structure of formula (XIII)

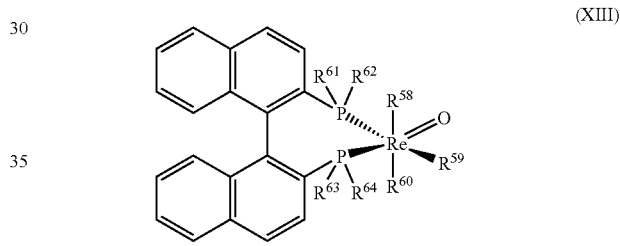

(XIII)

wherein $R^{58}$, $R^{59}$ and $R^{60}$ are halide, and $R^{61}$ and $R^{62}$ are aryl.

45. The method of claim 1, wherein the transition metal complex has the structure of formula (XIV)

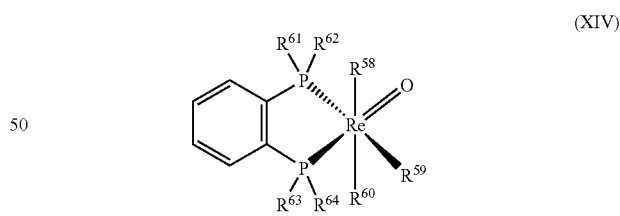

(XIV)

wherein $R^{58}$, $R^{59}$ and $R^{60}$ are halide, and $R^{61}$, $R^{62}$, $R^{63}$ and $R^{64}$ are aryl, or wherein $R^{61}$ and $R^{62}$, and/or $R^{63}$ and $R^{64}$, may be taken together to form a cyclic group.

* * * * *